United States Patent
Farmer

(10) Patent No.: US 8,097,247 B2
(45) Date of Patent: *Jan. 17, 2012

(54) PROBIOTIC, LACTIC ACID-PRODUCING BACTERIA AND USES THEREOF

(75) Inventor: Sean Farmer, Miami Beach, FL (US)

(73) Assignee: Ganeden Biotech, Inc., Mayfield Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/897,590

(22) Filed: Oct. 4, 2010

(65) Prior Publication Data

US 2011/0020305 A1 Jan. 27, 2011

Related U.S. Application Data

(63) Continuation of application No. 12/148,965, filed on Apr. 23, 2008, now Pat. No. 7,807,151, which is a continuation of application No. 11/305,507, filed on Dec. 16, 2005, now Pat. No. 7,708,988, which is a continuation of application No. 10/264,745, filed on Oct. 4, 2002, now abandoned, which is a continuation of application No. 09/370,793, filed on Aug. 5, 1999, now Pat. No. 6,461,607.

(60) Provisional application No. 60/097,594, filed on Aug. 24, 1998.

(51) Int. Cl.
*C12N 1/20* (2006.01)
*C12P 1/04* (2006.01)

(52) U.S. Cl. .................... 424/93.46; 424/93.1; 435/170; 435/243; 435/252.5; 514/2.3

(58) Field of Classification Search ............... 424/93.46; 435/170, 243, 252.5; 514/2.3
See application file for complete search history.

(56) References Cited

U.S. PATENT DOCUMENTS

| | | | |
|---|---|---|---|
| 3,091,572 A | 5/1963 | Luedemann et al. | |
| 4,110,477 A | 8/1978 | Naruse et al. | |
| 4,144,346 A | 3/1979 | Heeres et al. | |
| 4,321,258 A | 3/1982 | Dunlap | |
| 4,323,651 A | 4/1982 | Long et al. | |
| 4,695,546 A | 9/1987 | Aiba et al. | |
| 4,756,913 A | 7/1988 | Khorkova et al. | |
| 4,956,177 A | 9/1990 | King et al. | |
| 4,980,180 A | 12/1990 | Cully et al. | |
| 5,021,344 A | 6/1991 | Armau et al. | |
| 5,079,164 A | 1/1992 | Kirkovits et al. | |
| 5,102,800 A | 4/1992 | Hirikoshi | |
| 5,176,911 A | 1/1993 | Tosi et al. | |
| 5,200,336 A | 4/1993 | Kong et al. | |
| 5,266,315 A | 11/1993 | Taguchi et al. | |
| 5,413,960 A | 5/1995 | Dobrogosz et al. | |
| 5,439,678 A | 8/1995 | Dobrogosz et al. | |
| 5,439,995 A | 8/1995 | Bailly et al. | |
| 5,531,988 A | 7/1996 | Paul | |
| 5,534,253 A | 7/1996 | Casas et al. | |
| 5,665,354 A | 9/1997 | Neyra et al. | |
| 5,785,990 A | 7/1998 | Langrehr | |
| 6,132,710 A | 10/2000 | Panigrahi et al. | |
| 6,461,607 B1 | 10/2002 | Farmer | |
| 6,531,126 B2 | 3/2003 | Farmer | |
| 6,723,326 B1 | 4/2004 | Farmer | |
| 6,849,256 B1 * | 2/2005 | Farmer ...................... | 424/93.46 |
| 7,374,753 B1 | 5/2008 | Farmer et al. | |
| 7,807,151 B2 | 10/2010 | Farmer | |
| 2003/0031659 A1 | 2/2003 | Farmer | |
| 2006/0099197 A1 | 5/2006 | Farmer | |
| 2008/0233104 A1 | 9/2008 | Farmer | |
| 2011/0020306 A1 | 1/2011 | Farmer | |

FOREIGN PATENT DOCUMENTS

| | | |
|---|---|---|
| DE | 4132296 C1 | 12/1992 |
| GB | 1040278 A | 8/1966 |
| JP | 6483025 A | 3/1989 |
| JP | 4082827 A | 3/1992 |
| WO | WO-8905849 A1 | 6/1989 |
| WO | WO-9314187 A1 | 7/1993 |
| WO | WO-9411492 A1 | 5/1994 |

(Continued)

OTHER PUBLICATIONS

Allos, B.M., "Association between *Campylobacter* Infection and Guillain-Barré Syndrome", *J. Infect. Dis.* 176: S125-S128 (1997).

(Continued)

*Primary Examiner* — Ruth Davis
(74) *Attorney, Agent, or Firm* — Mintz Levin Cohn Ferris Glovsky and Popeo, P.C.

(57) ABSTRACT

The present invention discloses compositions and methodologies for the utilization of probiotic organisms in therapeutic compositions. More specifically, the present invention relates to the utilization of one or more species or strains of lactic acid-producing bacteria, preferably strains of *Bacillus coagulans*, for the control of gastrointestinal tract pathogens, including antibiotic-resistant gastrointestinal tract pathogens, and their associated diseases by both a reduction in the rate of colonization and the severity of the deleterious physiological effects of the colonization of the antibiotic-resistant pathogen. In addition, the present invention relates to the utilization of therapeutic compounds comprised of lactic acid-producing bacteria and anti-microbial agents such as antibiotics, anti-fungal compounds, anti-yeast compounds, or anti-viral compounds. The present invention also discloses methodologies for: (i) the selective breeding and isolation of probiotic, lactic acid-producing bacterial strains which possess resistance or markedly decreased sensitivity to anti-microbial agents (e.g., antibiotics, anti-fungal agents, anti-yeast agents, and anti-viral agents); and (ii) treating or preventing bacteria-mediated infections of the gastrointestinal tract by use of the aforementioned probiotic bacterial strains with or without the concomitant administration of antibiotics. While the primary focus is on the treatment of gastrointestinal tract infections, the therapeutic compositions of the present invention may also be administered to buccal, vaginal, optic, and like physiological locations.

10 Claims, 4 Drawing Sheets

FOREIGN PATENT DOCUMENTS

| WO | WO-9611014 A1 | 4/1996 |
|----|---------------|--------|
| WO | WO-9729762 A1 | 8/1997 |
| WO | WO-9734615 A1 | 9/1997 |
| WO | WO-9854982 A1 | 12/1998 |

OTHER PUBLICATIONS

Baker, et al., "Growth Requirements of 94 Strains of Thermophilic Bacilli", *Can. J. Microbiol* ., 6:557-563 (1960).
Barefoot et al., "Antibiosis Revisited: Bacteriocins Produced by Dairy Starter Cultures", *J. Diary Sci.*, 76:2366-2379 (1993).
Bernet, M.F. et al., "Adhesion of Human Bifidobacterial Strains to Cultured Human Intestinal Epithelial Cells and Inhibition of Enteropathogen-Cell Interactions" *Appl. Environ. Microbiol* . 59(12): 4121-4128 (1993).
Bernet, M.F. et al., "*Lactobacillus acidophilus* LA 1 binds to cultured human intestinal cell lines and inhibits cell attachment and cell invasion by enterovirulent bacteria", *Gut*, 35: 483-489 (1994).
Black, R.E. et al., "Experimental *Campylobacter jejuni* Infection in Humans" *J. Infect. Dis*. 157(3): 472-479 (1988).
Blaser, M.J. et al., "The Influence of Immunity on Raw Milk-Associated *Campylobacter* Infection", *JAMA*, 257(1):43-46 (1987).
Blaser, M.J., "Campylobacter Species" In: Principles and Practice of Infectious Diseases, Eds. Mandell et al., Churchill Livingstone Inc., New York, NY 3:1649-1658 (1990).
Challa, A. et al., "*Bifidobacterium longum* and lactulose suppress azoxymethane-induced colonic aberrant crypt foci in rats", *Carcinogenesis*, 18(3): 517-521 (1997).
Christi et al., "Role of dietary sulphate in the regulation of methanogenesis in the human large intestine", Gut, 33:1234-1238 (1992).
Cometta, et al., "*Escherichia coli* Resistant to Fluoroquinolones in Patients with Cancer and Neutropenia", *New Engl. J. Med.*, 330:1240-1241 (1994).
Database WPI, Section Ch, Week 198918, Derwent Publications Ltd., AN 1989-136223 XP002130556 & JP 01 083025 A (Hayashi), Mar. 28, 1989, Abstract.
Database WPI, Section Ch, Week 199637, Derwent Publications Ltd., AN 1996-368043 XP002130557 & JP 08 175921 A (Idemitsu Kosan Co., Ltd.), Jul. 9, 1996, Abstract.
De Simone, C. et al., "Effect of *Bifidobacterium bifidum* and *Lactobacillus acidophilus* on gut mucosa and peripheral blood B lymphocytes", *Immunopharmacol. Immunotoxicol.* 14(1&2): 331-340 (1992).
Elmer et al, "Biotherapeutic Agents: A Neglected Modality for the Treatment and Prevention of Selected Intestinal and Vaginal Infections", *JAMA*, 275(11):870-876 (1996).
Famularo, G. et al., "Stimulation of Immunity by Probiotics" In: Probiotics 2: Applications and Practical Aspects, Ed. R. Fuller, Boundary Row, London 133-161 (1997).
Fernandez, et al., "Effect of Diatomaceous Earth as an Anthelnimtic Treatment on Internal Parasites and Feedlot Performance of Beef Steers" *Animal Science* 66(3):635-641(1998).
Fuller, R., "Probiotics in Man and Animals" *J. Appl. Bacteriol.*, 66:365-378 (1989).
Gandhi, "*Lactobacillus sporogenes*: An Advancement in *Lactobacillus* Therapy", *Townsend Lett. Doctors & Patients*, 150:108-110 (1996).
Gibson, et al., "Selective Stimulation of Bifidobacteria in the Human Colon by Oligofructose and Inulin" *Gastroenterology*, 106:975-982 (1995).
Girardin et al., "Antimicrobial Activity of Food borne *Paeibacillus* and *Bacillus* spp. against *Clostridium botulinum*", *Journal of Food Protection*, 65(5): 806-813 (2002).
Gorbach, S., "Lactic Acid Bacteria and Human Health", *Ann. Med.*, 22:37-41 (1990).
Hata, et al., "Meningitis caused by *Bifidobacterium* in an infant" *Pediatr. Infect. Dis*., 7: 669-671 (1988).
Hill & Embil, "Vaginitis: current microbiologic and clinical concepts" *Can. Med. Assoc. J.*, 134: 321-331 (1986).
Jacobs-Reitsma, W.F. et al., "The induction of quinolone resistance in *Campylobacter* bacteria in broilers by *quinolone* treatment" In: Campylobacter, Helicobacters, and related organisms, Eds. Newell, et al. New York, NY 307-11 (1996).
Ketley, J.M., "Pathogenesis of Enteric Infection by *Campylobacter*", *Microbiology*, 143:5-21 (1997).
Klaenhammer, T., "Genetics of bacteriocins produced by lactic acid bacteria", *FEMS Microbiol. Rev.*, 12:39-85 (1993).
Koo, M.B. et al, "Long-Term Effect of Bifidobacteria and Neosugar on Precursor Lesions of Colonic Cancer in $Cf_1$ Mice" *Nutrit. Rev.*, 16:249-257 (1991).
Korshunov et al. "Effect of the Combined Administration of Antibiotic Resistant Bifidobacteria and the Corresponding Antibiotics on the Survival or Irradiated Mice", *Zh. Mikrobiol. Epidemol. Immunobiol.*, (5):50-53 (1982) Abstract Only.
Lidbeck et al., "Lactobacilli, anticarcinogenic activities and human intestinal microflora", *Eur. J. Cancer Prev.*, 1:341-353 (1992).
Malin et al., "Promotion of IgA Immune Response in Patients with Crohn's Disease by Oral Bacteriotherapy with *Lactobacillus* GG", *Ann. Nutr. Metab.*, 40:137-145 (1996).
Marsh, "Antimicrobial Strategies in the Prevention of Dental Caries", *Caries Res.*, 27:72-76 (1993).
Matsumara, K. et al., "Interferon Induction by Murine Peritoneal Macrophage Stimulated with *Lactobacillus gassen*" *Animal Sci. Technol. (Jpn)* 63:1157-1159 (1992).
Metchinikoff, E., "Prolongation of Life", Ed. P C Michell, G. P. Putnam's Sons, New York, NY, pp. 39-93, 132-183 (1910).
Mitchell, "Rearming in the Fight Against Bacteria" *Lancet*, 352:462-463 (1998).
Murphy, G.S. et al., "Ciprofloxacin- and Azithromycin-Resistant *Campylobacter* Causing Traveler's Diarrhea in U.S. Troops Deployed to Thailand in 1994" *Clin. Infect. Dis.*, 22:868-869 (1996).
Nakamura, et al., "Taxonomic study for *Bacillus coagulans* Hammer 1915" *J. Systematic Bacterio.*, 38:63-73 (1988).
Perdigon et al, "Symposium: Probiotic Bacteria for Humans: Clinical Systems for Evaluation of Effectiveness", *J. Dairy Sci.*, 78:1597-1606 (1995).
Perlman, et al., "Persistent *Campylobacter jejuni* Infections in Patients Infected with Human Immunodeficiency Virus (HIV)" *Ann. Intern. Med*., 108:540-546 (1988).
Peterson, M.C., "Conferences and Review: Clinical Aspects of *Campylobacter jejuni* Infections in Adults", *Wes. J. Med.*, 161(2):148-152 (1994).
Peterson, M.C., "Rheumatic Manifestations of *Campylobacter jejuni* and *C. fetus* Infections in Adults", *Scand. J. Rheumatol.*, 23:167-170 (1994).
Piddock, L.V., "Review: Quinolone resistance and *Campylobacter* supp." *J. Antimicrob. Chemother.*, 36:891-898 (1995).
Rafter, "The Role of Lactic Acid Bacteria in Colon Cancer Prevention", *Scand. J. Gastroenterol.*, 30:497-502 (1995).
Reddy, B.S. et al., "Inhibitory Effect of *Bifidobacterium longum* on Colon, Mammary, and Liver Carcinogenesis Induced by 2-Amino-3-methylimidazo[4,5-*f*]quinoline, a Food Mutagen", *Cancer Res.*, 53:3914-3918 (1993).
Reid, et al, "Is There a Role for *Lactobacilli* in Prevention of Urogenital and Intestinal Infections?" *Clin. Microbiol. Rev.*, 3:335-344 (1990).
Rowland, I.R. et al, "Degradation of *N*-Nitrosamines by Intestinal Bacteria", *Appl. Microbiol.*, 29: 7-12 (1975).
Rychen et al., "Effects of Three Microbial Probiotics on Postprandial Porto-arterial Concentration Differences of Glucose, Galactose and Amino-Nitrogen in the Young Pig" *British Journal of Nutrition*, 74:19-26 (1995).
Saavedra, "Feeding of Bifidobacterium bifidum and *Streptococcus thermophilus* to Infants in Hospital for Prevention of Diarrhoea and Shedding of Rotavirus" *Lancet*, 344:1046-109 (1994).
Salminen et al, "Clinical uses of Probiotics for Stabilizing the Gut Mucosal Barrier: Successful Strains and Future Challenges", *Antoine Van Leeuwenhoek*, 70:347-358 (1996).
Schiffrin, E.J. et al., "Immune modulation of blood leukocytes in humans by lactic acid bacteria: criteria for strain selection", *Am. J. Clin. Nutr*,. 66:515S-520S (1997).
Sekine, K. et al., "Induction and Activation of Tumoricidal Cells In Vivo and In Vitro by the Bacterial Cell Wall of *Bifidobacterium infantis*" *Bifidobacteria and Microflora* 13: 65-77 (1994).

Shannon, "Multiple-antibiotic-resistant salmonella" *Lancet*, 352:490-491 (1998).

Shoenfeld, Y. et al., "Guillain-Barré as an Autoimmune Disease" *Int. Arch. Allergy Immunol.* 109:318-326 (1996).

Smith, K.E., et al., "Fluoroquinolone-resistant *Campylobacter* isolated from humans and poultry in Minnesota", *International Conference on Emerging Infectious Diseases*; Mar. 8-11, 1998.

Sneath, P.H.A. et al., *Bergey's Manual of Systematic Bacteriology*, Eds. Sneath et al., *Williams and Wilkons*, Baltimore, MD (2):1117 (1986).

Solis-Pereyra, et al., "Induction of Human Cytokines by Bacteria Used in Dairy Foods". *Nutr. Res.* 13:1127-1140 (1993).

Sorvillo, F.J. et al., "Incidence of Campylobacteriosis Among Patients with AIDS in Los Angeles County", *J. Acquired Immune Defic. Syndr.*, 4:598-602 (1991).

Standiford, et al, "Lipoteichoic Acid Induces Secretion of Interleukin-8 from Human Blood Monocytes: a Cellular and Molecular Analysis", *Infect. Linmun,*. 62:119-125 (1994).

Sussman, et al., "Clinical manifestations and therapy of *Lactobacillus endocarditis*: report of a case and review of the literature" *Rev Infect. Dis.*, 8: 771-776 (1986).

Tauxe, R.V. "Epidemiology of *Campylobacter jejuni* infections in the United States and other industrial nations" In: *Campylobacter jejuni*: current and future trends, Eds. Nachamkin et al., American Society for Microbiology, Washington, DC 9-13 (1992).

Thomason, et al, "Bacterial vaginosis: current review with indications for asymptomatic therapy" *Am. J. Obstet Gynecol.*, 165:1210-1217 (1991).

Tojo, M., "The Effects of *Bifidobacterium breve* Administration on Campylobacter Enteritis", *Acta Pediatr. Jpn.* 29:160-167 (1987).

Winberg, et al., "Pathogenesis of urinary tract infection-experimental studies of vaginal resistance to colonization" *Ped. Nephrol.*, 7: 509-514 (1993).

WindHolz, et al., *The Merck Index*, Tenth Edition, 549 (1983).

Yamazaki, S. et al., "Protective Effect of Bifidobacterium-Monoassociation against Lethal Activity of *Escherichia coli*" *Bifidobacteria microflora* 1: 55-59 (1982).

Zhang, X.B. et al., "Antimutagenicity and Binding of Lactic Acid Bacteria from a Chinese Cheese to Mutagenic Pyrolyzates", *J. Dairy Sci.*, 73: 2702-2710 (1990).

Kim et al., "Development of *Lactobacillus-sporogenes* Resistant to Rifampicin an Antituberculosis Agent" (Abstract Only), Korean J. Micro. 27(2): 155-161, (1989).

\* cited by examiner

| Characteristic | *Bacillus coagulans* Response |
|---|---|
| Catalase production | Yes |
| Acid from D-Glucose | Yes |
| Acid from L-Arabinose | Variable |
| Acid from D-Xylose | Variable |
| Acid from D-Mannitol | Variable |
| Gas from Glucose | Yes |
| Hydrolysis of Casein | Variable |
| Hydrolysis of Gelatin | No |
| Hydrolysis of Starch | Yes |
| Utilization of Citrate | Variable |
| Utilization of Propionate | No |
| Deamidation of Tyrosine | No |
| Degradation of Phenylalanine | No |
| Nitrate reduced to Nitrite | Variable |
| Allatoin or Urate Required | No |

Fig. 1

| Mycotic Pathogen | Associated Disease | Inhibition Results |
|---|---|---|
| *T. mentagrophytes* (ATCC No. 4808) | Tinea pedis (Athlete's Foot) | Excellent |
| *T. interdigitabe* (ATCC No. 9129) | Tinea pedis (Athlete's Foot) | Excellent |
| *T. mentagrophytes* (ATCC No. 36107) | Tinea versicolor (Ring Worm) | Excellent |
| *T. mentagrophytes* (ATCC No. 8125) | Tinea barbae (Face & Neck Inflammation) | Good |
| *T. mentagrophytes* (ATCC No. 9533) | Tinea pedis (Athlete's Foot) | Excellent |
| *T. mentagrophytes* (ATCC No. 28187) | Tinea pedis (Athlete's Foot) | Excellent |
| *T. rubrum* (ATCC No. 18753) | Mild Dermatophytosis | Good |
| *T. yaoundei* (ATCC No. 13947) | Ring Worm, Scalp | Good |

Fig. 2

| Species | Pathology | Inhibition Results |
|---|---|---|
| *Candida abbicans* (ATCC No. 26555) | Chronic Mucocutaneous, Candidiasis, Myositis and Thymoma | Excellent |
| *C. albicans* (ATCC No. 44203) | Systemic Candidiasis | Excellent |
| *C. albicans* (ATCC No. 44807) | Yeast and Mycelial Phase | Excellent |
| *C. tropicauis* (ATCC No. 62377) | Cervical Yeast Infection | Excellent |

Fig. 3

Formulation 1: *Cephalosporin*
| | |
|---|---|
| *Bacillus coagulans* | $1 \times 10^9$ spores (10 mg) |
| Cefaclor (antibiotic) | 250 mg |
| Fructo-oligosaccharides (FOS) | 90 mg |
| Total | 350 milligrams |

Formulation 2: *Macrolide*
| | |
|---|---|
| *Bacillus coagulans* | $1 \times 10^9$ spores (10 mg) |
| Azithromycin (antibiotic) | 250 milligrams |
| Micro-crystalline cellulose | 90 mg |
| Total | 350 mg |

Formulation 3: *Penicillin Family*
| | |
|---|---|
| *Bacillus Coagulans* | $1 \times 10^9$ spores (10 mg) |
| Ampicillin (antibiotic) | 250 mg |
| Fructo-oligosaccharides (FOS) | 240 mg |
| Total | 500 mg |

Formulation 4: *Penicillin Family (Augmentin)*
| | |
|---|---|
| *Bacillus coagulans* | $1 \times 10^9$ spores (10 mg) |
| Amoxacillin (antibiotic) | 200 mg |
| Clavulanate | 31.25 mg |
| Magnesium sterate | 73.75 mg |
| Total | 350 mg |

Formulation 5: *Fluoroquinolone*
| | |
|---|---|
| *Bacillus coagulans* | $1 \times 10^9$ spores (10 mg) |
| Ciprofloxacin (antibiotic) | 250 mg |
| Magnesium citrate | 10 mg |
| Micro-crystalline cellulose | 80 mg |
| Total | 350 mg |

Formulation 6: *Vancomycin*
| | |
|---|---|
| *Bacillus coagulans* | $1 \times 10^9$ spores (10 mg) |
| Vancomycin (antibiotic) | 250 mg |
| Micro-crystalline cellulose | 90 mg |
| Total | 350 mg |

PROBIOTIC, LACTIC ACID-PRODUCING BACTERIA AND USES THEREOF

RELATED APPLICATIONS

This application is a continuation of U.S. Ser. No. 12/148,965 filed on Apr. 23, 2008 (now U.S. Pat. No. 7,807,151), which is a continuation of U.S. Ser. No. 11/305,507, filed Dec. 16, 2005 (now U.S. Pat. No. 7,708,988), which is a continuation of U.S. Ser. No. 10/264,745, filed on Oct. 4, 2002 (abandoned), which is a continuation application of U.S. Ser. No. 09/370,793, filed on Aug. 5, 1999 (now U.S. Pat. No. 6,461,607), which claims priority to U.S. Ser No. 60/097,594 filed on Aug. 24, 1998, abandoned, the contents of each of these applications are herein incorporated by reference in their entirety.

FIELD OF THE INVENTION

The present invention relates to methods and compositions for the utilization of probiotic organisms in therapeutic compositions. More specifically, the present invention relates to the utilization of one or more species or strains of lactic acid-producing bacteria, preferably strains of *Bacillus coagulans*, for the control of gastrointestinal tract pathogens, including antibiotic-resistant gastrointestinal tract pathogens, and their associated diseases by both a reduction in the rate of colonization and the severity of the deleterious physiological effects of the colonization of the antibiotic-resistant pathogen. In addition, the present invention relates to the utilization of therapeutic compounds comprised of lactic acid-producing bacteria and anti-microbial agents such as antibiotics, anti-fungal compounds, anti-yeast compounds, or anti-viral compounds. In addition, the present invention relates to the use of lactic acid-producing bacteria in animals to mitigate gastrointestinal tract pathogens.

BACKGROUND OF THE INVENTION

1. Probiotic Microorganisms

The gastrointestinal microflora has been shown to play a number of vital roles in maintaining gastrointestinal tract function and overall physiological health. For example, the growth and metabolism of the many individual bacterial species inhabiting the gastrointestinal tract depend primarily upon the substrates available to them, most of which are derived from the diet. See e.g., Gibson G. R. et al., 1995. *Gastroenterology* 106: 975-982; Christi, S. U. et al., 1992. *Gut* 33: 1234-1238. These finding have led to attempts to modify the structure and metabolic activities of the community through diet, primarily with probiotics which are live microbial food supplements. The best known probiotics are the lactic acid-producing bacteria (i.e., *Lactobacilli*) and *Bifidobacteria*, which are widely utilized in yogurts and other dairy products. These probiotic organisms are non-pathogenic and non-toxigenic, retain viability during storage, and survive passage through the stomach and small intestine. Since probiotics do not permanently colonize the host, they need to be ingested regularly for any health promoting properties to persist. Commercial probiotic preparations are generally comprised of mixtures of *Lactobacilli* and *Bifidobacteria*, although yeast such as *Saccharomyces* have also been utilized.

Probiotic preparations were initially systematically evaluated for their effect on health and longevity in the early-1900's (see e.g., Metchinikoff, E., *Prolongation of Life*, Willaim Heinermann, London 1910), although their utilization has been markedly limited since the advent of antibiotics in the 1950's to treat pathological microbes. See e.g., Winberg, et al, 1993. *Pediatr. Nephrol.* 7: 509-514; Malin et al, *Ann. Nutr. Metab.* 40: 137-145; and U.S. Pat. No. 5,176,911. Similarly, lactic acid-producing bacteria (e.g., *Bacillus, Lactobacillus* and *Streptococcus* species) have been utilized as food additives and there have been some claims that they provide nutritional and/or therapeutic value. See e.g., Gorbach, 1990. *Ann. Med.* 22: 37-41; Reid et al, 1990. *Clin. Microbiol. Rev.* 3: 335-344.

Therefore, probiotic microorganisms are those which confer a benefit when grow in a particular environment, often by inhibiting the growth of other biological organisms in the same environment. Examples of probiotic organisms include bacteria and bacteriophages which possess the ability to grow within the gastrointestinal tract, at least temporarily, to displace or destroy pathogenic organisms, as well as providing other benefits to the host. See e.g., Salminen et al, 1996. *Antonie Van Leeuwenhoek* 70: 347-358; Elmer et al, 1996. *JAMA* 275: 870-876; Rafter, 1995. *Scand. J. Gastroenterol.* 30: 497-502; Perdigon et al, 1995. *J. Dairy Sci.* 78: 1597-1606; Gandi, *Townsend Lett. Doctors & Patients*, pp. 108-110, January 1994; Lidbeck et al, 1992. *Eur. J. Cancer Prev.* 1:341-353.

The majority of previous studies on probiosis have been observational rather than mechanistic in nature, and thus the processes responsible for many probiotic phenomena have yet to be quantitatively elucidated. Some probiotics are members of the normal colonic microflora and are not viewed as being overtly pathogenic. However, these organisms have occasionally caused infections (e.g., bacteremia) in individuals who are, for example, immunocompromised. See e.g., Sussman, J. et al., 1986. *Rev Infect. Dis.* 8: 771-776; Hata, D. et al., 1988. *Pediatr. Infect. Dis.* 7: 669-671.

While the attachment of probiotics to the gastrointestinal epithelium is an important determinant of their ability to modify host immune reactivity, this is not a universal property of *Lactobacilli* or *Bifidobacteria*, nor is it essential for successful probiosis. See e.g., Fuller, R., 1989. *J. Appl. Bacteriol.* 66: 365-378. For example, adherence of Lactobacillus acidophilus and some *Bifidobacteria* to human enterocyte-like CACO-2 cells has been demonstrated to prevent binding of enterotoxigenic and enteropathogenic *Escherichia coli*, as well as *Salmonella typhimurium* and *Yersinia pseudotuberculosis*. See e.g., Bernet, M. F. et al., 1994. *Gut* 35: 483-489; Bernet, M. F. et al., 1993. *Appl. Environ. Microbiol.* 59: 4121-4128.

While the gastrointestinal microflora presents a microbial-based barrier to invading organisms, pathogens often become established when the integrity of the microbiota is impaired through stress, illness, antibiotic treatment, changes in diet, or physiological alterations within the G.I. tract. For example, *Bifidobacteria* are known to be involved in resisting the colonization of pathogens in the large intestine. See e.g., Yamazaki, S. et al., 1982. *Bifidobacteria and Microflora* 1: 55-60. Similarly, the administration of *Bifidobacteria breve* to children with gastroenteritis eradicated the causative pathogenic bacteria (i.e., *Campylobacter jejuni*) from their stools (see e.g., Tojo, M., 1987. *Acta Pediatr. Jpn.* 29: 160-167) and supplementation of infant formula milk with *Bifidobacteria bifidum* and *Streptococcus thermophilus* was found to reduce rotavirus shedding and episodes of diarrhea in children who were hospitalized (see e.g., Saavedra, J. M., 1994. *The Lancet* 344: 1046-109.

In addition, some lactic acid producing bacteria also produce bacteriocins which are inhibitory metabolites which are responsible for the bacteria's anti-microbial effects. See e.g., Klaenhammer, 1993. *FEMS Microbiol. Rev.* 12: 39-85; Barefoot et al., 1993. *J. Diary Sci.* 76: 2366-2379. For example, selected *Lactobacillus* strains which produce antibiotics have been demonstrated as effective for the treatment of infections, sinusitis, hemorrhoids, dental inflammations, and various other inflammatory conditions. See e.g., U.S. Pat. No. 5,439,995. Additionally, *Lactobacillus reuteri* has been shown to produce antibiotics which possess anti-microbial activity against Gram negative and Gram positive bacteria, yeast, and various protozoan. See e.g., U.S. Pat. Nos. 5,413,960 and 5,439,678.

Probiotics have also been shown to possess anti-mutagenic properties. For example, Gram positive and Gram negative bacteria have been demonstrated to bind mutagenic pyrolysates which are produced during cooking at a high temperature. Studies performed with lactic acid-producing bacteria has shown that these bacteria may be either living or dead, due to the fact that the process occurs by adsorption of mutagenic pyrolysates to the carbohydrate polymers present in the bacterial cell wall. See e.g., Zang, X. B. et al., 1990. *J. Dairy Sci.* 73: 2702-2710. *Lactobacilli* have also been shown to degrade carcinogens (e.g., N-nitrosamines), which may serve an important role if the process is subsequently found to occur at the level of the mucosal surface. See e.g., Rowland, I. R. and Grasso, P., *Appl. Microbiol.* 29: 7-12. Additionally, the co-administration of lactulose and Bifidobacteria longum to rats injected with the carcinogen azoxymethane was demonstrated to reduce intestinal aberrant crypt foci, which are generally considered to be pre-neoplastic markers. See e.g., Challa, A. et al., 1997. *Carcinogenesis* 18: 5175-21. Purified cell walls of *Bifidobacteria* may also possess anti-tumorigenic activities in that the cell wall of *Bifidobacteria infantis* induces the activation of phagocytes to destroy growing tumor cells. See e.g., Sekine, K. et al., 1994. *Bifidobacteria and Microflora* 13: 65-77. *Bifidobacteria* probiotics have also been shown to reduce colon carcinogenesis induced by 1,2-dimethylhydrazine in mice when concomitantly administered with fructo-oligosaccharides (FOS; see e.g., Koo, M. B., and Rao, A. V., 1991. *Nutrit. Rev.* 51: 137-146), as well as inhibiting liver and mammary tumors in rats (see e.g., Reddy, B. S., and Rivenson, A., 1993. *Cancer Res.* 53: 3914-3918).

It has also been demonstrated that the microbiota of the gastrointestinal tract affects both mucosal and systemic immunity within the host. See e.g., Famularo, G. et al., Stimulation of Immunity by Probiotics. In: *Probiotics: Therapeutic and Other Beneficial Effects.* pg. 133-161. (Fuller, R., ed. Chapman and Hall, 1997). The intestinal epithelial cells, blood leukocytes, B- and T-lymphocytes, and accessory cells of the immune system have all been implicated in the aforementioned immunity. See e.g., Schiffrin, E. J. et al., 1997. *Am. J. Clin. Nutr.* 66(suppl): 5-20S. Other bacterial metabolic products which possess immunomodulatory properties include: endotoxic lipopolysaccharide, peptidoglycans, and lipoteichoic acids. See e.g., Standiford, Tex., 1994. *Infect. Linmun.* 62: 119-125. Accordingly, probiotic organisms are thought to interact with the immune system at many levels including, but not limited to: cytokine production, mononuclear cell proliferation, macrophage phagocytosis and killing, modulation of autoimmunity, immunity to bacterial and protozoan pathogens, and the like. See e.g., Matsumara, K. et al., 1992. *Animal Sci. Technol. (Jpn)* 63: 1157-1159; Solis-Pereyra, B. and Lemmonier, D., 1993. *Nutr. Res.* 13: 1127-1140. *Lactobacillus* strains have also been found to markedly effect changes in inflammatory and immunological responses including, but not limited to, a reduction in colonic inflammatory infiltration without eliciting a similar reduction in the numbers of B- and T-lymphocytes. See e.g., De Simone, C. et al., 1992. *Immunopharmacol. Immunotoxicol.* 14: 331-340.

2. Gastrointestinal Effects of Antibiotic Administration

Antibiotics are widely used to control pathogenic microorganisms in both humans and animals. Unfortunately, the widespread use of anti-microbial agents, especially broad spectrum antibiotics, has resulted in a number of serious clinical consequences. For example, antibiotics often kill beneficial, non-pathogenic microorganisms (i.e., flora) within the gastrointestinal tract which contribute to digestive function and health. Accordingly, relapse (the return of infections and their associated symptoms) and secondary opportunistic infections often result from the depletion of lactic acid-producing and other beneficial flora within the gastrointestinal tract.

Unfortunately, most, if not all, lactic acid-producing or probiotic bacteria are extremely sensitive to common antibiotic compounds. Accordingly, during a normal course of antibiotic therapy, many individuals develop a number of deleterious physiological side-effects including: diarrhea, intestinal cramping, and sometimes constipation. These side-effects are primarily due to the non-selective action of antibiotics, as antibiotics do not possess the ability to discriminate between beneficial, non-pathogenic and pathogenic bacteria, both bacterial types are killed by these agents. Thus, individuals taking antibiotics offer suffer from gastrointestinal problems as a result of the beneficial microorganisms (i.e., intestinal flora), which normally colonize the gastrointestinal tract, being killed or severely attenuated. The resulting change in the composition of the intestinal flora can result in vitamin deficiencies when the vitamin-producing intestinal bacteria are killed, diarrhea and dehydration and, more seriously, illness should a pathogenic organism overgrow and replace the remaining beneficial gastrointestinal bacteria.

Another deleterious result of indiscriminate use of anti-microbial agents is the generation of multiple antibiotic-resistant pathogens. See e.g., Mitchell, P. 1998. *The Lancet* 352: 462-463; Shannon, K., 1998. *Lancet* 352: 490-491. The initial reports of meticillin-resistant *Staphylococcus aurous* (MRSA) infections have been over-shadowed by the more recent outbreaks of vancomycin-resistant *Enterococci* (VRE). The development of such resistance has led to numerous reports of systemic infections which remained untreatable with conventional antibiotic therapies. Recently, a vancomycin—(generally regarded as an antibiotic of "last resort") resistant strain of *Staphylococcus aurous* was responsible for over 50 deaths in a single Australian hospital. See e.g., Shannon, K., 1998. *Lancet* 352: 490-491.

*Enterococci* are currently a major nosocomial pathogen and are likely to remain as such for a long period of time. *Enterococci*, as well as other microbes, obtain antibiotic resistance genes in several different ways. For example, *Enterococci* emit pheromones which cause them to become "sticky" and aggregate, thus facilitating the exchange of genetic material, such as plasmids (autonomously replicating, circular DNA which often carry the antibiotic resistance genes). In addition, some *Enterococci* also possess "conjugative transposons" which are DNA sequences that allow them to directly transfer resistance genes without plasmid intermediary. It is believed that penicillin resistance has been conferred from *Enterococci* to *Streptococci* to *Staphylococci* through this later mechanism.

Since 1989, a rapid increase in the incidence of infection and colonization with vancomycin-resistant *Enterococci* (VRE) has been reported by numerous hospitals within the United States. This increase poses significant problems, including: (i) the lack of available anti-microbial therapy for VRE infections, due to the fact that most VRE are also resistant to the drugs which were previously used to treat such infections (e.g., Aminoglycosides and Ampicillin); and (ii) the possibility that the vancomycin-resistant genes present in VRE can be transferred to other gram-positive microorganisms (e.g., *Staphylococcus aureus*).

An increased risk for VRE infection and colonization has also been associated with previous vancomycin and/or multi-anti-microbial therapy, severe underlying disease or immunosuppression, and intra-abdominal surgery. Because *Enterococci* can be found within the normal gastrointestinal and female genital tracts, most enterococcal infections have been attributed to endogenous sources within the individual patient. However, recent reports of outbreaks and endemic infections caused by Enterococci, including VRE, have indicated that patient-to-patient transmission of the microorganisms can occur through either direct contact or through indirect contact via (i) the hands of personnel; or (ii) contaminated patient-care equipment or environmental surfaces.

Accordingly, there remains a need for a highly efficacious biorational therapy which functions to mitigate the deleterious physiological effects of digestive pathogens, including antibiotic-resistant gastrointestinal tract pathogens, in both humans and animals, by the colonization (or re-colonization) of the gastrointestinal tract with probiotic microorganisms, following the administration of antibiotics, anti-fungal, anti-viral, and similar agents. Additionally, a need as remains for the development of a highly efficacious biorational therapy which functions to mitigate antibiotic-resistant digestive pathogens, in both humans and animals, by the colonization (or re-colonization) of the gastrointestinal tract with probiotic microorganisms, following the administration of antibiotics, anti-fungal, anti-viral, and similar agents, by functioning to reduce both the colonization rate and the potential physiologically deleterious effects due to the colonization of antibiotic-resistant digestive pathogens.

SUMMARY OF THE INVENTION

The present invention discloses methodologies for the selective breeding and isolation of antibiotic-resistant, lactic acid-producing bacterial strains for utilization in various types of therapeutic applications. For example, in one specific embodiment, these lactic acid-producing bacteria are co-administered with one or more anti-microbial compounds (e.g., antibiotics, anti-mycotic compounds, anti-viral compounds, and the like). It should be noted that, in most clinical and scientific fields, the production or evolution of antibiotic resistant microorganisms is an undesirable consequence of unnecessary issue and/or improper use of antibiotics compounds. However, the present invention serves to constructively produce bacteria that possess resistance to a single, as opposed to multiple, antibiotics.

In another related aspect, the present invention discloses compositions and methodologies for the utilization of these compositions comprising non-pathogenic, probiotic lactic acid-producing bacteria which are used to mitigate the deleterious physiological effects of gastrointestinal tract pathogens, including antibiotic-resistant gastrointestinal tract pathogens, in both humans and animals, by the colonization (or more-correctly, re-colonization) of the gastrointestinal tract with probiotic microorganisms, following the administration of antibiotics, anti-fungal, anti-viral, and similar agents.

Additionally, the present invention relates to the use of lactic acid-producing bacteria to mitigate the effects of parasites and pathogens in animals.

1. Co-Administration of Probiotic bacterial with Anti-Microbial Compounds

It has been demonstrated that common and antibiotic resistant digestive pathogens can be controlled with the utilization of particular probiotic organisms that have been identified for their ability to remain viable in the gastrointestinal tract during antibiotic therapy. However, it should be noted that, prior to the disclosure of the present invention, most strains of probiotic bacteria (e.g., *Lactobacillus, Bifidiobacterium,* and *Bacillus*) were found to be sensitive to the majority of antibiotics, hence they were not particularly suitable for co-administration with broad-spectrum antibiotics.

Accordingly, in the present invention, strains of *Bacillus coagulans* were isolated and identified for their ability to remain viable when exposed to typical therapeutic concentrations of antibiotics that are commonly used to mitigate digestive pathogens. These new *Bacillus* variants disclosed herein may be administered prior to, concomitantly with, or subsequent to the administration of antibiotics. In a preferred embodiment, these *Bacillus* strains are co-administered in combination with the selected antibiotic which they are resistant to.

One probiotic bacterial strain disclosed by the present invention is *Bacillus coagulans* GB-M—a new variant or mutant of Bacillus coagulans ATCC No. 31284. *Bacillus coagulans* GB-M has been demonstrated to be resistant to Macrolide antibiotics such as Azithromycin, Erythromycin and other similar antibiotic compounds. The advantages of using a biological in combination with a chemical antibiotic or the concurrent use of a biological with a chemical serves to address the many hazards and side effects of antibiotic therapy. In addition, the use of these aforementioned variants, as well as other lactic acid-producing biorationals, in combination with chemotherapy drugs and anti-fungal would be of great benefit to those taking these compounds, due to the fact that these individuals, more often than not, suffer from side effects which are a direct result of depleted "normal" gastrointestinal flora.

In addition to the aforementioned aspects of the present invention, the utilization of bifidogenic oligosaccharides (e.g., fructo-oligosaccharides (FOS)) are beneficial to facilitate the re-establishment and proliferation of other beneficial lactic acid-producing bacteria and to further promote gastrointestinal microbial biodiversity. In one embodiment of the present invention, a composition comprising an isolated and specific antibiotic resistant Bacillus coagulans strain in combination with an effective amount of a fructo-oligosaccharide (FOS) in a pharmaceutically acceptable carrier suitable for administration to the gastrointestinal track of a human or animal is disclosed. In preferred embodiments of the present invention, the Bacillus coagulans strain is included in the composition in the form of spores, a dried cell mass, in the form of a flowable concentrate, or in the form of a stabilized gel or paste.

In another embodiment of the present invention, the *Bacillus coagulans* strain is combined with a therapeutically-effective dose of an antibiotic. In preferred embodiments of the present invention, the *Bacillus coagulans* strain is combined with a therapeutic concentration of antibiotic including, but not limited to: Gentamicin; Vancomycin; Oxacillin; Tetracyclines; Nitroflurantoin; Chloramphenicol; Clindamycin; Trimethoprim-sulfamethoxasole; a member of the Cephlosporin antibiotic family (e.g., Cefaclor, Cefadroxil, Cefixime, Cefprozil, Ceftriaxone, Cefuroxime, Cephalexin, Loracarbef, and the like); a member of the Penicillin family of antibiotics (e.g., Ampicillin, Amoxicillin/Clavulanate, Bacampicillin, Cloxicillin, Penicillin VK, and the like); with a member of the Fluoroquinolone family of antibiotics (e.g., Ciprofloxacin, Grepafloxacin, Levofloxacin, Lomefloxacin, Norfloxacin, Ofloxacin, Sparfloxacin, Trovafloxacin, and the like); or a member of the Macrolide antibiotic family (e.g., Azithromycin, Erythromycin, and the like).

Similarly, a therapeutically-effective concentration of an anti-fungal agent may also be utilized. Such anti-fungal agents include, but are not limited to: Clotrimazole, Fluconazole, Itraconazole, Ketoconazole, Miconazole, Nystatin, Terbinafine, Terconazole, and Tioconazole.

The aforementioned embodiment involves selectively-culturing the probiotic bacteria (which may initially be sensitive to the antibiotic of choice) in gradually increasing concentrations of antibiotic in order to facilitate the development of decreased antibiotic sensitivity or, preferably, total antibiotic resistance. It should be noted that this is the most preferred embodiment of the present invention due to the fact that current FDA (and other governmental agency) regulations expressly prohibit the intentional release of recombinant antibiotic resistant bacterial strains into the environment. Hence, the utilization of the antibiotic resistant strains of bacteria disclosed in the present invention, produced through non-recombinant methodologies, would not be violative of these aforementioned regulations.

Similarly, further embodiments of the present invention discloses methodologies for the generation of antibiotic-resistant strains of lactic acid-producing bacteria by microbial genetic- and recombinant DNA-based techniques. With respect to the microbial genetic-based methodology antibiotic resistance may be conferred by the "transfer" of genetic information from an antibiotic resistant bacterial strain to an antibiotic sensitive bacterial strain through plasmid- and non-plasmid-mediated genetic transfer. Plasmids are small, non-chromosomal, autonomously replicating, circular DNA which often carry the antibiotic resistance genes. For example, in one embodiment of the present invention, conjugative transposons (i.e., DNA sequences that allow the direct transfer of resistance genes without a plasmid intermediary) may be utilized to confer antibiotic resistance to an antibiotic sensitive bacterial stain. In another embodiment, recombinant DNA-based, plasmid-mediated methodologies may also be utilized.

These novel, antibiotic resistant bacterial isolates will then be used in combination with an appropriate antibiotic for the mitigation of pathogen-associated disease and/or the re-establishment of normal digestive flora following the administration of antibiotics and/or other agents which deplete the gastrointestinal ecology. Hence, the present invention demonstrates that all antibiotic compounds possess the ability to work synergistically with an antibiotic-resistant biorational to increase the overall efficacy of antibiotic administration, while concomitantly mitigating deleterious side-effects.

In another embodiment of the present invention, the beneficial, antibiotic resistant, lactic acid-producing bacterial strain is co-administered with an anti-fungal agent and/or an antibiotic so as to ameliorate the growth of both the mycotic and/or bacterial pathogen. In addition, anti-viral agents, as well as agents which inhibit the growth of yeast may also be utilized, with or without the concomitant administration of an antibiotic.

In yet another embodiment of the present invention, the administration of the beneficial, lactic acid-producing bacterial strain is, by way of example but not of limitation, topical, vaginal, intra-ocular, intra-nasal, intra-otic, buccal, and the like.

2. Use of Probiotic Bacteria to Inhibit Colonization of Antibiotic-Resistant Gastrointestinal Pathogens Additionally disclosed herein are compositions and methods of treatment which exploit the novel discovery that specific, lactic acid-producing bacteria (e.g., *Bacillus coagulans*) possess the ability to exhibit inhibitory activity in preventing and reducing the colonization rates of gastrointestinal bacterial infections, particularly those infections associated with antibiotic resistant pathogens such as *Enterococccus, Clostridium, Escherichia,* and *Staphylococcus* species, as well as mitigating the deleterious physiological effects of the infection by the pathogen. Exceptionally hardy or enteric-coated lactic acid-producing bacterium are preferably used, with spore-forming *Bacillus* species, particularly *Bacillus coagulans,* being a preferred embodiment. The present invention also discloses therapeutic compositions, therapeutic systems, and methods of use for the treatment and/or prevention of various pathogenic bacterial gastrointestinal tract infections, particularly those infections associated with antibiotic-resistant pathogens.

In one embodiment of the present invention, a therapeutic composition comprising a viable, non-pathogenic lactic acid-producing bacterium, preferably *Bacillus coagulans*, in a pharmaceutically-acceptable carrier suitable for oral administration to the gastrointestinal tract of a human or animal, is disclosed. In another embodiment, a *Bacillus coagulans* strain is included in the therapeutic composition in the form of spores. In another embodiment, a *Bacillus coagulans* strain is included in the composition in the form of a dried cell mass.

In another aspect of the present invention, a composition s comprising an extracellular product of a lactic acid-producing bacterial strain, preferably *Bacillus coagulans*, in a pharmaceutically-acceptable carrier suitable for oral administration to a human or animal, is disclosed. In a preferred embodiment, the extracellular product is a supernatant or filtrate of a culture of an isolated *Bacillus coagulans* strain.

Another aspect of the invention is a method of preventing or treating a bacterial gastrointestinal infection in a human, comprising the steps of orally administering to a human subject a food or drink formulation containing viable colony forming units of a non-pathogenic lactic acid bacterium, preferably a *Bacillus* species and more preferably an isolated *Bacillus coagulans* strain, and allowing the bacteria to grow in the human subject's gastrointestinal tract.

In one embodiment of the aforementioned method, the step of allowing the non-pathogenic bacteria to grow, further includes inhibiting growth of antibiotic-resistant *Candida* species, *Staphylococcus* species, *Streptococcus* species, *Proteus* species, *Pseudomonas* species, *Escherichia coli, Clostridium* species, *Klebsiella* species, and *Enterococccus* species. In a preferred embodiment, the method inhibits antibiotic-resistant *Pseudomonas aeruginosa, Staphylococcus aureus, Staphylococcus pyogenes, Clostridium perfingens, Clostridium difficile, Clostridium botulinum, Clostridium tributrycum, Clostridium sporogenes, Enterococccus faecalis, Enterococccus faecium,* and various other significant species of antibiotic gastrointestinal pathogens or combinations thereof.

One aspect of the invention is a lactic acid-producing bacterial composition comprising an isolated *Bacillus* species strain, combined with a pharmaceutically-acceptable carrier suitable for oral administration to a human or animal, wherein the isolated Bacillus species strain is capable of growing at temperatures of about 30° C. to about 65° C., produces L(+)

dextrorotatory lactic acid, produces spores resistant to heat up to 90° C., and exhibits competitive, antibiotic, or parasitical activity that inhibits or reduces the colonization rate of the pathogenic bacteria associated with gastroenteritis and other significant digestive pathogens. The probiotic activity primarily results from vegetative growth of the isolated *Bacillus* species strain in the gastrointestinal tract of a human or animal. This growth causes a direct competition with the pathogenic bacteria, as well as producing an acidic, non-hospitable environment. In yet another embodiment, the probiotic activity results from an extracellular product of the isolated lactic acid-producing strain produced within the gastrointestinal. The present invention also discloses a therapeutic system for treating, reducing or controlling gastrointestinal bacterial infections, particularly infections associated with antibiotic-resistant pathogens.

The present invention provides several advantages. In particular, insofar as there is a detrimental effect to the use of antibiotics because of the potential to produce antibiotic-resistant microbial species, it is desirable to have an anti-microbial therapy which does not utilize conventional anti-microbial agents. Hence, the present invention does not contribute to the production of future generations of antibiotic-resistant pathogens.

3. Use of Probiotic Bacteria in Animals

It has now been discovered that parasites and pathogens colonizing the intestinal tract of animals can be inhibited and/or controlled by the use of diatomaceous earth in combination with the use of a probiotic lactic acid producing bacteria.

The present invention describes compositions, therapeutic systems, and methods of use for inhibiting pathogen and/or parasite growth in the gastrointestinal tract and feces of animals. A composition of this invention comprises an effective amount of diatomaceous earth in combination with a non-pathogenic lactic acid-producing bacteria, with spore-forming *Bacillus* species, particularly *Bacillus coagulans*, being a preferred embodiment.

According to the invention, there is provided a composition comprising diatomaceous earth in combination with a lactic acid-producing bacteria in a pharmaceutically- or nutritionally-acceptable carrier suitable for oral administration to the digestive tract of an animal. In one embodiment of the composition, a *Bacillus coagulans* strain is included in the composition in the form of spores. In another embodiment, a *Bacillus coagulans* strain is included in the composition in the form of a dried cell mass. In another embodiment, a *Bacillus coagulans* strain is included in the composition in the form of a stabilized paste. In another embodiment, a *Bacillus coagulans* strain is included in the composition in the form of stabilized gel. In another embodiment, a *Bacillus coagulans* strain is included in the composition in the form of a stabilized liquid suspension.

In one embodiment, the invention contemplates a composition comprising diatomaceous earth comprised predominantly of the Melosira genus, preferably at least 80%. In one embodiment, the bacterial is present in the composition at a concentration of approximately $1\times10^3$ to $1\times10^{14}$ colony forming units (CFU)/gram, preferably approximately $1\times10^5$ to $1\times10^{12}$ CFU/gram, whereas in other preferred embodiments the concentrations are approximately $1\times10^9$ to $1\times10^{13}$ CFU/gram, approximately $1\times10^5$ to $1\times10^7$ CFU/g, or approximately $1\times10^8$ to $1\times10^9$ CFU/gram.

In one embodiment, the bacteria is in a pharmaceutically acceptable carrier suitable for oral administration to an animal, preferably, as a powdered food supplement, a variety of pelletized formulations, or a liquid formulation. In one embodiment, the composition further includes an effective amount of a bifidogenic oligosaccharide, such as a short or long chain fructo-oligosaccharide (FOS), a gluco-oligosaccharide (GOS) or other long-chain oligosaccharide polymer not readily digested by pathogenic bacteria as described herein.

The invention also describes a therapeutic system for inhibiting pathogen and/or parasite growth in the gastrointestinal tract and/or feces of an animal comprising a container comprising a label and a composition as described herein, wherein said label comprises instructions for use of the composition for inhibiting pathogen and/or parasite growth.

It should be understood that both the foregoing general description and the following detailed description are exemplary and explanatory only and are not restrictive of the present invention as claimed.

DESCRIPTION OF THE FIGURES

FIG. 1 illustrates, in tabular form, a summary of the metabolic growth characteristics and requirements of *Bacillus coagulans*.

FIG. 2 illustrates, in tabular form, the ability of *Bacillus coagulans* to inhibit various fungal pathogens, of the *Trichophyton* species, using an in vitro assay. The ATCC Accession Numbers of each fungal strain of the *Trichophyton* species from the American Type Culture Collection (ATCC) are also enumerated herein.

FIG. 3 illustrates, in tabular form, the ability of *Bacillus coagulans* to inhibit various yeast pathogens, of the *Candida* species, using an in vitro assay. The ATCC Accession Numbers of each yeast strain of the *Candida* species from the American Type Culture Collection (ATCC) are also enumerated herein.

FIG. 4 illustrates, in tabular form, Formulations 1-6 of the therapeutic compositions of the present invention.

DETAILED DESCRIPTION OF THE INVENTION

Unless defined otherwise, all scientific and technical terms used herein have the same meaning as commonly understood by those skilled in the relevant art. Unless mentioned otherwise, the techniques employed or contemplated herein are standard methodologies well known to one of ordinary skill in the art. The examples of embodiments are for illustration only.

The present invention is discloses the recent discovery that non-pathogenic, lactic acid-producing bacterial species (i.e., "probiotic bacteria"), such as the exemplary Bacillus coagulans, may be utilized in combination with antibiotic compounds or other functional anti-microbial drugs and supplements so as to form therapeutic compositions for use in ameliorating and/or controlling the colonization of pathogenic bacteria with the gastrointestinal tract of both humans and animals. In addition, these non-pathogenic, lactic-producing, probiotic bacteria may be co-administered with an anti-fungal agent and/or an antibiotic to ameliorate the growth of the mycotic or bacterial pathogen in question. In brief, the present invention utilizes antibiotic-resistant, non-pathogenic bacteria to mitigate the growth and subsequent establishment of antibiotic-resistant, pathogenic microbes within, for example, the gastrointestinal tract. Also disclosed herein are various therapeutic compositions, methods for using said therapeutic compositions, and systems for containing and administering/delivering said therapeutic compositions.

In addition, the present invention the present invention also discloses compositions and methodologies for the utilization of these compositions, comprising non-pathogenic, probiotic lactic acid-producing bacteria, in the mitigation of the deleterious physiological effects of gastrointestinal tract pathogens, including antibiotic-resistant gastrointestinal tract pathogens, in both humans and animals, by the colonization (or more-correctly, re-colonization) of the gastrointestinal tract with probiotic microorganisms, following the administration of antibiotics, anti-fungal, anti-viral, and similar agents.

1. Antibiotic Administration and Biorational Therapy

Antibiotics are widely used to control pathogenic microorganisms in both humans and animals. Unfortunately, the indiscriminate use of these agents has led to the generation of pathogenic bacteria which frequently exhibit resistance to multiple antibiotics. In addition, the administration of antibiotics often results in the killing of many of the beneficial microorganisms (i.e., flora) within the gastrointestinal tract which contribute to "normal" gastrointestinal function (e.g., digestion, absorption, vitamin production, and the like). Accordingly, relapse (the return of infections and their associated symptoms) and secondary opportunistic infections often result from the depletion of Lactobacillus and other types of beneficial microbial flora within the gastrointestinal tract. Unfortunately, most, if not all, lactic acid-producing or probiotic bacteria are extremely sensitive to common antibiotic compounds. Therefore, during a normal course of antibiotic therapy, many individuals develop a number of deleterious physiological side-effects including: diarrhea, intestinal cramping, and sometimes constipation. These side-effects are primarily due to the non-selective action of antibiotics, as antibiotics do not possess the ability to discriminate between beneficial bacteria and pathogenic bacteria. Hence, both pathogenic and non-pathogenic bacteria are killed by these agents.

A biorational therapy that includes an antibiotic and an appropriate microorganism that is resistant to the selected antibiotic would serve to enhance the efficacy of the antibiotic (if the antibiotic is used for the purpose of controlling a gastrointestinal tract pathogen) and assist in providing a digestive environment which is conducive to the reestablishment of the endogenous lactic acid bacteria and suppress the growth of pathogens.

It should also be noted that the present invention is not limited solely to oral administration of the therapeutic compounds disclosed herein. For example, antibiotic and anti-fungal resistance is also associated with topical and intra-vaginal medications. Thus, in an additional embodiment, the co-administration of a lactic acid or other beneficial bacterial culture with a vaginal anti-fungal medication would effectively aid in the mitigation of the mycotic or bacterial pathogen in question and repopulate the vagina and reduce the incidence of relapse. It should be noted that it has been demonstrated that the absence of lactic acid-producing bacteria within the vagina is the most common etiology of vaginal yeast infections and bacterial vaginosis.

In an additional embodiment, skin creams, lotions, gels and the like could similarly contain a beneficial biorational component that would be effective in controlling pathogenic organisms on the skin and further reduce the emergence of antibiotic resistant pathogens. By way of example, but not of limitation, the cells, spores or extracellular materials from such beneficial biorational bacteria could be incorporated into these skin products for this express purpose. Burn patients usually are given antibiotics to reduce the incidence of opportunistic infection. Pathogenic *Pseudomonas, Staphylococcus*, and/or *Enterococci* are frequently associated with infections of severe burns. Hence, the salves, lotions, gels and the like combined with the beneficial, biorational microorganisms or their extracellular products, as disclosed in the present invention, would be effective in achieving a state of proper biodiversity to the skin in burn cases, as, generally, such biodiversity is not associated with pathogenic overgrowth.

A further embodiment of the present invention involves the utilization of probiotic organisms in livestock production, in which antibiotics such as Vancomycin and Gentamicin are commonly used to stimulate health and weight gain. Most, if not all, probiotic organisms are sensitive to these two antibiotics and this fact has limited the potential use of such microorganisms in the livestock industry. In addition, there are many environmentally-related problems associated with the use of antibiotics in livestock production. For example, antibiotic laden animal waste degrades very slowly and the antibiotic residue can persist, further slowing biodegradation. With the addition of species of bacteria that are resistant to Vancomycin, Gentamicin, and other antibiotics, biodegradation could actually be enhanced.

2. Probiotic, Lactic Acid-Producing Bacterial Strains

A biorational therapy which includes an antibiotic and an appropriate microorganism that is resistant to the selected antibiotic serves to both enhance the overall therapeutic efficacy of the antibiotic (if the antibiotic is used for the purpose of controlling a digestive pathogen) and to assist in providing a gastrointestinal environment that is conducive to the reestablishment of the endogenous lactic acid-producing bacteria and to suppress the concomitant growth of pathogenic microorganisms.

As utilized herein, "probiotic" refers to microorganisms that form at least a part of the transient or endogenous flora and thereby exhibit a beneficial prophylactic and/or therapeutic effect on the host organism. Probiotics are generally known to be clinically safe (i.e., non-pathogenic) by those individuals skilled in the art. By way of example, and not of limitation to any particular mechanism, the prophylactic and/or therapeutic effect of a lactic acid-producing bacteria of the present invention results, in part, from a competitive inhibition of the growth of pathogens due to: (i) their superior colonization abilities; (ii) parasitism of undesirable microorganisms; (iii) the production of lactic acid and/or other extracellular products possessing anti-microbial activity; or (iv) various combinations thereof. It should be noted that the aforementioned products and activities of the lactic acid-producing bacteria of . the present invention act synergistically to produce the beneficial probiotic effect disclosed herein.

A probiotic bacteria which is suitable for use in the methods and compositions of the present invention: (i) possesses the ability to produce lactic acid; (ii) demonstrates beneficial function within the gastrointestinal tract; and is non-pathogenic. By way of example and not of limitation, many suitable bacteria have been identified and are described herein, although it should be noted that the present invention is not to be limited to currently-classified bacterial species insofar as the purposes and objectives as disclosed. The physiochemical results from the in vivo production of lactic acid is key to the effectiveness of the probiotic lactic acid-producing bacteria of the present invention. Lactic acid production markedly decreases the pH (i.e., increases acidity) within the local micro-floral environment and does not contribute to the growth of many undesirable, physiologically-deleterious bacteria and fungi. Thus, by the mechanism of lactic acid production, the probiotic inhibits growth of competing pathogenic bacteria.

Typical lactic acid-producing bacteria useful as a probiotic of this invention are efficient lactic acid producers which include non-pathogenic members of the Bacillus genus which produce bacteriocins or other compounds which inhibit the growth of pathogenic organisms. Exemplary lactic acid-producing, non-pathogenic *Bacillus* species include, but are not limited to: *Bacillus coagulans; Bacillus coagulans* Hammer; and *Bacillus brevis* subspecies *coagulans*.

Exemplary lactic acid-producing Lactobacillus species include, but are not limited to: Lactobacillus acidophilus, Lactobacillus casei, *Lactobacillus DDS*-1, *Lactobacillus GG, Lactobacillus rhamnosus, Lactobacillus plantarum, Lactobacillus reuteri, Lactobacillus gasserii, Lactobacillus jensenii, Lactobacillus delbruekii, Lactobacillus, bulgaricus, Lactobacillus salivarius* and *Lactobacillus sporogenes* (also designated as *Bacillus coagulans*).

Exemplary lactic acid-producing *Sporolactobacillus* species include all *Sporolactobacillus* species, for example, *Sporolactobacillus* P44.

Exemplary lactic acid-producing *Bifidiobacterium* species include, but are not limited to: *Bifidiobacterium adolescentis, Bifidiobacterium animalis, Bifidiobacterium bifidum, Bifidiobacterium bifidus, Bifidiobacterium breve, Bifidiobacterium infantis, Bifidiobacterium infantus, Bifidiobacterium longum*, and any genetic variants thereof.

Several *Bacillus* species which are preferred in the practice of the present invention, include, but are not limited to the lactic acid-producing *Bacillus coagulans* and *Bacillus laevolacticus*. Various other non-lactic acid-producing *Bacillus* species may be utilized in the present invention so long as they produce compounds which possess the ability to inhibit pathogenic bacterial or mycotic growth. Examples of such suitable non-lactic acid-producing Bacillus include, but are not limited to: *Bacillus subtilis, Bacillus uniflagellatus, Bacillus lateropsorus, Bacillus laterosporus BOD, Bacillus megaterium, Bacillus polymyxa, Bacillus licheniformis, Bacillus pumilus*, and *Bacillus sterothermophilus*. Other strains that could be employed due to probiotic activity include members of the *Streptococcus (Enterococcus)* genus. For example, *Enterococcus faecium*, is commonly used as a livestock probiotic and, thus, could be utilized as a co-administration agent. It should be noted that, although exemplary of the present invention, *Bacillus coagulans* is only utilized herein as a model for various other acid-producing (e.g., lactic acid) species of probiotic bacteria which may be useful in the practice of the present invention, and therefore is not to be considered as limiting. Furthermore, it is also intended that any of the acid-producing species of probiotic or nutritional bacteria can be used in the compositions, therapeutic systems and methods of the present invention.

The *Bacillus* species, particularly those species having the ability to form spores (e.g., *Bacillus coagulans*), are a preferred embodiment of the present invention. The ability to sporulate makes these bacterial species relatively resistant to heat and other conditions, provides for a long shelf-life in product formulations, and is deal for survival and colonization of tissues under conditions of pH, salinity, and the like within the gastrointestinal tract. Moreover, additional useful properties of many *Bacillus* species include being non-pathogenic, aerobic, facultative and heterotrophic, thus rendering these bacterial species safe and able to readily colonize the gastrointestinal tract.

Exemplar methods and compositions are described herein using *Bacillus coagulans* ATCC No. 31284 (and new variants or mutants thereof) as a probiotic. Purified Bacillus coagulans is particularly useful as a probiotic in the present invention as it is generally accepted that the various "classic" *Lactobacillus* and/or *Bifidiobacterium* species are unsuitable for colonization of the gut due to their instability in the highly acidic environment of the gastrointestinal tract, particularly the human gastrointestinal tract. In contrast, the preferred *Bacillus* species of the present invention are able to survive and colonize the gastrointestinal tract in a highly efficacious manner. Additionally, probiotic *Bacillus coagulans* is non-pathogenic and is generally regarded as safe (i.e., GRAS classification) by the U.S. Federal Drug Administration (FDA) and the U.S. Department of Agriculture (USDA), and by those individuals skilled within the art.

Because *Bacillus coagulans* possesses the ability to produce heat-resistant spores, it is particularly useful for making pharmaceutical compositions which require heat and pressure in their manufacture. Accordingly, formulations that include the utilization viable *Bacillus coagulans* spores in a pharmaceutically-acceptable carrier are particularly preferred for making and using compositions disclosed in the present invention.

The growth of these various *Bacillus* species to form cell cultures, cell pastes, and spore preparations is generally well-known within the art. It should be noted that the exemplary culture and preparative methods which are described herein for Bacillus coagulans may be readily utilized and/or modified for growth and preparation of the other (lactic) acid-producing bacteria disclosed in the present invention.

3. Characteristics and Sources of *Bacillus Coagulans*

The Gram positive rods of *Bacillus coagulans* have a cell diameter of greater than 1.0 µm with variable swelling of the sporangium, without parasporal crystal production. *Bacillus coagulans* is a non-pathogenic, Gram positive, spore-forming bacteria that produces L(+) lactic acid (dextrorotatory) under homo-fermentation conditions. It has been isolated from natural sources, such as heat-treated soil samples inoculated into nutrient medium (see e.g., *Bergey's Manual of Systemic Bacteriology*, Vol. 2,Sneath, P. H. A. et al., eds., Williams & Wilkins, Baltimore, Md., 1986). Purified *Bacillus coagulans* strains have served as a source of enzymes including endonucleases (e.g., U.S. Pat. No. 5,200,336); amylase (U.S. Pat. No. 4,980,180); lactase (U.S. Pat. No. 4,323,651) and cyclo-malto-dextrin glucano-transferase (U.S. Pat. No. 5,102,800). *Bacillus coagulans* has also been utilized to produce lactic acid (U.S. Pat. No. 5,079,164). A strain of *Bacillus coagulans* (also referred to as *Lactobacillus sporogenes*; Sakaguti & Nakayama, ATCC No. 31284) has been combined with other lactic acid producing bacteria and *Bacillus natto* to produce a fermented food product from steamed soybeans (U.S. Pat. No. 4,110,477). *Bacillus coagulans* strains have also been used as animal feeds additives for poultry and livestock to reduce disease and improve feed utilization and, therefore, to increase growth rate in the animals (International PCT Pat. Applications No. WO 9314187 and No. WO 9411492). In particular, *Bacillus coagulans* strains have been used as general nutritional supplements and agents to control constipation and diarrhea in humans and animals.

The purified *Bacillus coagulans* bacteria utilized in the present invention are available from the American Type Culture Collection (ATCC, Rockville, Md.) using the following accession numbers: *Bacillus coagulans* Hammer NRS 727 (ATCC No. 11014); *Bacillus coagulans* Hammer strain C (ATCC No. 11369); *Bacillus coagulans* Hammer (ATCC No. 31284); and *Bacillus coagulans* Hammer NCA 4259 (ATCC No. 15949). Purified *Bacillus coagulans* bacteria are also available from the Deutsche Sarumlung von Mikroorganismen and Zellkuturen GmbH (Braunschweig, Germany) using the following accession numbers: *Bacillus coagulans* Hammer 1915 (DSM No. 2356); *Bacillus coagulans* Hammer 1915 (DSM No. 2383, corresponds to ATCC No. 11014); *Bacillus coagulans* Hammer (DSM No. 2384,corresponds to ATCC No. 11369); and *Bacillus coagulans* Hammer (DSM No. 2385, corresponds to ATCC No. 15949). *Bacillus coagulans* bacteria can also be obtained from commercial suppliers such as Sabinsa Corporation (Piscataway, N.J.) or K.K. Fermentation (Kyoto, Japan).

These aforementioned *Bacillus coagulans* strains and their growth requirements have been described previously (see e.g., Baker, D. et al, 1960. *Can. J. Microbiol.* 6: 557-563; Nakamura, H. et al, 1988. *Int. J. Svst. Bacteriol.* 38: 63-73. In addition, various strains of *Bacillus coagulans* can also be isolated from natural sources (e.g., heat-treated soil samples) using well-known procedures (see e.g., *Bergey's Manual of Systemic Bacteriology*, Vol. 2, p. 1117, Sneath, P. H. A. et al., eds., Williams & Wilkins, Baltimore, Md., 1986).

It should be noted that *Bacillus coagulans* had previously been mis-characterized as a *Lactobacillus* in view of the fact that, as originally described, this bacterium was labeled as *Lactobacillus sporogenes* (See Nakamura et al. 1988. *Int. J. Syst, Bacteria* 38: 63-73). However, initial classification was incorrect due to the fact that *Bacillus coagulans* produces spores and through metabolism excretes L(+)-lactic acid, both aspects which provide key features to its utility. Instead, these developmental and metabolic aspects required that the bacterium be classified as a lactic acid *bacillus*, and therefore it was re-designated. In addition, it is not generally appreciated that classic *Lactobacillus* species are unsuitable for colonization of the gut due to their instability in the harsh (i.e., acidic) pH environment of the bile, particularly human bile. In contrast, *Bacillus coagulans* is able to survive and colonize the gastrointestinal tract in the bile environment and even grown in this low pH range. In particular, the human bile environment is different from the bile environment of animal models, and heretofore there has not been any accurate descriptions of *Bacillus coagulans* growth in human gastrointestinal tract models.

3.1 Culture of Vegetative *Bacillus Coagulans*

*Bacillus coagulans* is aerobic and facultative, and is typically cultured at pH 5.7 to 6.8, in a nutrient broth containing up to 2% (by wt) NaCl, although neither NaCl, nor KCl are required for growth. A pH of about 4.0 to about 7.5 is optimum for initiation of sporulation (i.e., the formation of spores). The bacteria are optimally grown at 30° C. to 45° C., and the spores can withstand pasteurization. Additionally, the bacteria exhibit facultative and heterotrophic growth by utilizing a nitrate or sulfate source. The metabolic characteristics of *Bacillus coagulans* are summarized in FIG. 1.

*Bacillus coagulans* can be cultured in a variety of media, although it has been demonstrated that certain growth conditions are more efficacious at producing a culture which yields a high level of sporulation. For example, sporulation is demonstrated to be enhanced if the culture medium includes 10 mg/l of $MgSO_4$ sulfate, yielding a ratio of spores to vegetative cells of approximately 80:20. In addition, certain culture conditions produce a bacterial spore which contains a spectrum of metabolic enzymes particularly suited for the present invention (i.e., production of lactic acid and enzymes for the enhanced probiotic activity and biodegradation). Although the spores produced by these aforementioned culture conditions are preferred, various other compatible culture conditions which produce viable *Bacillus coagulans* spores may be utilized in the practice of the present invention.

Suitable media for the culture of *Bacillus coagulans* include: PDB (potato dextrose broth); TSB (tryptic soy broth); and NB (nutrient broth), which are all well-known within the field and available from a variety of sources. In one embodiment of the present invention, media supplements which contain enzymatic digests of poultry and/or fish tissue, and containing food yeast are particularly preferred. A preferred supplement produces a media containing at least 60% protein, and about 20% complex carbohydrates and 6% lipids. Media can be obtained from a variety of commercial sources, notably DIFCO (Newark, N.J.); BBL (Cockeyesville, Md.); Advanced Microbial Systems (Shakopee, Minn.); and Troy Biologicals (Troy, Md.

In a preferred embodiment of the present invention, a culture of *Bacillus coagulans* Hammer bacteria (ATCC No. 31284) was inoculated and grown to a cell density of about $1 \times 10^8 - 10^9$ cells/ml in nutrient broth containing: 5.0 g Peptone; 3.0 g Meat Extract; 10-30 mg $MnSO_4$ and 1,000 ml distilled water, the broth was then adjusted to pH 7.0. The bacteria were cultured by utilization of a standard airlift fermentation vessel at 30° C. The range of $MnSO_4$ acceptable for sporulation was found to be 1.0 mg/l to 1.0 g/l. The vegetative bacterial cells can actively reproduce up to 65° C., and the spores are stable up to 90° C.

Following culture, the *Bacillus coagulans* Hammer bacterial cells or spores were collected using standard methods (e.g., filtration, centrifugation) and the collected cells and spores may subsequently be lyophilized, spray dried, air dried or frozen. As described herein, the supernatant from the cell culture can be collected and used as an extracellular agent secreted by *Bacillus coagulans* which possesses anti-microbial activity useful in a formulation of this invention.

A typical yield obtained from the aforementioned culture methodology is in the range of approximately $1 \times 10^9$ to $1 \times 10^{13}$ viable cells/spores and, more typically, approximately $1 \times 10^{11}$ to $1.5 \times 10^{11}$ cells/spores per gram prior to being dried. It should also be noted that the *Bacillus coagulans* spores, following a drying step, maintain at least 90% viability for up to 7 years when stored at room temperature. Hence, the effective shelf-life of a composition containing *Bacillus coagulans* Hammer spores at room temperature is approximately 10 years.

3.2 Preparation of *Bacillus Coagulans* Spores

Alternately, a culture of dried *Bacillus coagulans* Hammer bacteria (ATCC No. 31284) spores was prepared as follows. Approximately $1 \times 10^7$ spores were inoculated into one liter of culture medium containing: 24 g (wt./vol.) potato dextrose broth; 10 g of an enzymatic-digest of poultry and fish tissue; 5 g of fructo-oligosaccharides (FOS); and 10 g $MnSO_4$. The culture was maintained for 72 hours under a high oxygen environment at 37° C. so as to produce a culture having approximately $15 \times 10^{10}$ cells/gram of culture. The culture was then filtered to remove the liquid culture medium and the resulting bacterial pellet was resuspended in water and lyophilized. The lyophilized bacteria were ground to a fine "powder" by use of standard good manufacturing practice (GMP) methodologies.

It should be noted that the most preferred embodiment of the present invention utilizes *Bacillus coagulans* in spore, rather than vegetative bacterial form.

3.3 Preparation of *B. Coagulans* Extracellular Products

Although the primary focus of the present invention is upon the utilization of lactic acid-producing probiotic bacteria in the form of vegetative cells or spores, an additional embodiment utilizes extracellular products comprising a supernatant or filtrate of a culture of a *Bacillus coagulans* strain for the prevention and/or control of infections caused by bacterium, fungi, yeast, and virus, and combinations thereof. Extracellular products of *Bacillus coagulans* may also be included in compositions such as foods and liquids to be fed to infants.

One liter cultures of *Bacillus coagulans* was prepared as described in Section 5.1, except that the fructo-oligosaccharide (FOS) was omitted. The culture was maintained for 5 days as described, at which time FOS was added at a concentration of 5 g/liter, and the culture was continued. Subsequently, 20 ml of carrot pulp was then added at day 7, and the culture was harvested when the culture became saturated (i.e., no substantial cell division).

The culture was first autoclaved for 30 minutes at 250° F., and then centrifuged at 4000 r.p.m. for 15 mm. The resulting supernatant was collected and filtered in a Buchner funnel through a 0.8 µm filter. The filtrate was collected and further filtered through a 0.2 µm Nalge vacuum filter. The resulting final filtrate was then collected (an approximate volume of 900 ml) to form a liquid containing an extracellular product which may be further purified and/or quantitatively analyzed by use of various methodologies which are well-known within the art.

4 Bifidogenic Oligosaccharides

Bifidogenic oligosaccharides, as designated herein, are a class of carbohydrates particularly useful for preferentially promoting the growth of a lactic acid-producing bacteria of the present invention. These oligosaccharides include, but are not limited to: fructo-oligosaccharides (FOS); gluco-oligosaccharides (GOS); other long-chain oligosaccharide polymers of fructose and/or glucose; and the trisaccharide-raffinose. All of these aforementioned carbohydrates are not readily digested by pathogenic bacteria. Thus, the preferential growth of lactic acid-producing bacteria is promoted by the utilization of these bifidogenic oligosaccharides due to the nutrient requirements of this class of bacterium, as compared to pathogenic bacteria.

Bifidogenic oligosaccharides are long chain polymers that are utilized almost exclusively by the indigenous *Bifidobacteria* and *Lactobacillus* in the intestinal tract and can be similarly utilized by *Bacillus*. In contrast, physiologically deleterious bacteria such as *Clostridium, Staphylococcus, Salmonella* and *Escherichia coli* cannot metabolize FOS, or other bifidogenic oligosaccharides, and therefor use of these bifidogenic oligosaccharides in combination with a lactic acid-producing bacteria of the present, preferably *Bacillus coagulans*, allows these beneficial, probiotic bacteria to grow and effectively compete with, and eventually replace any undesirable, pathogenic microorganisms within the gastrointestinal tract.

The use of bifidogenic oligosaccharides in the compositions of the present invention provides a synergistic effect thereby increasing the effectiveness of the probiotic-containing compositions disclosed herein. This synergy is manifested by selectively increasing the ability of the probiotic bacterium to grow by, for example, increasing the level of nutrient supplementation which preferentially selects for growth of the probiotic bacteria over many other bacterial species within the infected tissue.

In addition, it is readily understood that *Bifidobacteria* and *Lactobacillus* are also producers of lactic acid. Bifidogenic oligosaccharides enable these aforementioned probiotic organisms to proliferate preferentially over the undesirable bacteria within the gastrointestinal tract, thereby augmenting the probiotic state of the body by further enhancing the solubility of these nutrients (whether of food origin or as a result of nutritional supplement augmentation). Thus, the presence of the bifidogenic oligosaccharides in the compositions of the present invention allows for more effective microbial inhibition by increasing the ability of all varieties of probiotic bacteria to grow, and therefore provide said benefit.

The bifidogenic oligosaccharide of the present invention may be used either alone, or in combination with a lactic acid-producing microorganisms in a therapeutic composition. More specifically, due to the growth promoting activity of bifidogenic oligosaccharides, the present invention contemplates a composition comprising a bifidogenic oligosaccharide present in a concentration sufficient to promote the growth of lactic acid-producing microorganisms. As shown herein, these concentrations amounts can vary widely, as the probiotic microorganisms will respond to any metabolic amount of nutrient oligosaccharide, and therefore the present invention need not be so limited.

A preferred and exemplary bifidogenic oligosaccharide is FOS, although other carbohydrates may also be utilized, either alone or in combination. FOS can be obtained from a variety of natural sources, including commercial suppliers. As a product isolated from natural sources, the components can vary widely and still provide the beneficial agent, namely FOS. FOS typically has a polymer chain length of from about 4 to 200 sugar units, with the longer lengths being preferred. For example, the degree of purity can vary widely so long as biologically-functional FOS is present in the final formulation. Preferred FOS formulations contain at least 50% by weight of fructo-oligosaccharides compared to simple(mono or disaccharide) sugars such as glucose, fructose or sucrose, preferably at least 80% fructo-oligosaccharides (FOS), more preferably at least 90% and most preferably at least 95% FOS. Sugar content and composition can be determined by any of a variety of complex carbohydrate analytical detection methods as is well known. Preferred sources of FOS include, but are not limited to: inulin; Frutafit IQ™ (Imperial Suiker Unie; Sugar Land, Tex.); NutraFlora™ (Americal Ingredients, Inc.; Anaheim, Calif.); and Fruittrimfat Replacers and Sweeteners (Emeryville, Calif.). Bifidogenic oligosaccharides such as GOS, and other long chain oligosaccharides are also available from commercial vendors.

5. Diatomaceous Earth

Diatomaceous earth is the skeletal remains of single cell aquatic plants known as diatoms which are typically relatively uniform in composition, depending upon the source of the deposit and the component species of diatoms present in the deposit. Diatomaceous earth is characterized as having a silica content, a characteristic morphological shape, depending upon the species, and an average size of from about 5 to 20 microns (µm) in diameter.

Different species of diatoms in diatomaceous earth provide a diverse range of shapes, providing different degrees of sharp and/or spiny edges which when contacted with insects, parasites and small microorganisms pierce the protective coatings of the target parasite/pathogen. Diatomaceous earth is included in a therapeutic composition of this invention in a wide variety of concentrations, depending upon the manner of administration. Typical compositions contain from about 0.1 to 99% weight of diatomaceous earth per weight (w/w) of composition. For concentrated single dose uses, a high content of diatomaceous earth is used, typically 5 to 50% w/w, and preferably about 5 to 10% w/w. For continuous feed applications, a moderate to low content of diatomaceous earth is used, typically 0.5 to 10% w/w, and preferably 1 to 5% w/w.

A preferred diatomaceous earth for use in a composition of the present invention has a low ash content, typically less than 1% w/w, a low amorphous silica content, typically less than 1% w/w, and a low volconoclastic sediment, typically less than 1% w/w. Insofar as a preferred diatomaceous earth has the further property of presenting sharp and/or spiny edges to damage the external protective surfaces of the parasite/pathogen to be inhibited. Diatom shapes are well characterized in art, and the spiny, sharp character can be easily observed by microscopic examination of the diatoms. By observation and quantitative analysis, one can readily determine the proportions of the component diatoms in the diatomaceous earth. A preferred diatomaceous earth contains a high content of abrasive diatoms. A particularly preferred diatomaceous earth contains Melosira diatoms, and preferably is comprised of at least 50% w/w Melosira diatoms, more preferably at least 70% w/w Melosira diatoms, and most preferably at least 80% Melosira diatoms.

Diatomaceous earth can be obtained from a variety of sources. Typically, any diatom deposit is a source of diatomaceous earth. Commercial suppliers routinely mine, characterize and provide different grades of diatomaceous earth. A particularly preferred supplier of diatomaceous earth rich in Melosira diatoms is the CR Minerals Corporation, Golden, Colo.

6. Methods of Producing or Enhancing Antibiotic Resistance

As previously discussed, the present invention discloses methodologies for the selection, isolation, and culturing of antibiotic-resistant strains of lactic acid-producing bacteria be used as concomitantly administered biorational agents. These embodiments may be predicated upon:
(i) selectively culturing the probiotic bacteria (which may initially be sensitive to the antibiotic of choice) in gradually increasing concentrations of antibiotic of choice in order to facilitate the development of decreased antibiotic sensitivity or, preferably, antibiotic resistance; (ii) utilizing "conjugative transposons" (i.e., DNA sequences that allow the direct transfer of resistance genes without a plasmid intermediary) to confer antibiotic resistance to an antibiotic sensitive bacterial stain; and (iii) utilizing plasmids (i.e., small, non-chromosomal, autonomously replicating, circular DNA which often naturally possess antibiotic resistance genes) possessing genes conferring resistance to the antibiotic of choice which are generated by standard Recombinant DNA-based techniques.

It should be noted, however, that the most preferred embodiment of the present invention utilizes the selective culturing of the probiotic bacteria in gradually increasing concentrations of antibiotic of choice in order to facilitate the development of decreased antibiotic sensitivity or, preferably, antibiotic resistance. This embodiment, which will be more fully discussed below, is preferred due to the fact that current FDA and other governmental agency regulations expressly prohibit the intentional release of "man-made" (e.g., recombinant) antibiotic resistant bacterial strains into the environment. Hence, the utilization of the antibiotic resistant strains of bacteria disclosed in the present invention, produced through the non-recombinant-based, selective culture-based methodology, would not be violative of these aforementioned regulations. It should be noted, however, that the preference of this embodiment is not intended to be limiting, but rather reflects current regulations governing this field of endeavor. Should these regulations be modified, or if new regulations are promulgated, the inventors fully intend to utilize all methodologies disclosed herein to practice the present invention in the most efficacious manner possible.

*Bacillus coagulans* (strain ATCC Accession No. 31284) was assayed for antibiotic resistance/sensitivity utilizing the Kirby-Bauer agar dilution method (see e.g., *Bergey's Manual of Systemic Bacteriology*, Vol. 2, Sneath, P. H. A. et al., eds., Williams & Wilkins, Baltimore, Md., 1986). This methodology demonstrated that this *Bacillus coagulans* strain was susceptible to Piperacillin, Trimethoprim-Sulfamethoxasole, Ampicillin, Ciprofloxacin, Erythromycin, Vancomycin, Gentamicin, and Oxacillin and was intermediate with respect to Clindamycin and Tetracycline. Specifically, by Vitek, the MICs were found to be: (i) Ampicillin—2; (ii) Penicillin G—0.12; (iii) Vancomycin—<0.5; (iv) Nitrofurantoin—<32; (v) Norfioxacin—<4; (vi) Chloramphenicol—8; (vii) Clindamycin—>8 (resistant); and Tetracycline—>16 (resistant). *Bacillus coagulans* (strain ATCC Accession No. 31284) possesses natural resistance to the antibiotics Clindamycin and Tetracycline.

Subsequently, each prospective microorganism was then screened, utilizing the aforementioned methodology, for antibiotic sensitivity. Media and agars which were specific for each prospective bacteria were mixed with sub-lethal levels of the desired antibiotic compound. For example, DIFCO Trypticase Soy Agar (TSA) containing a sub-lethal level of Vancomycin was prepared. The media/antibiotic mixture was then sterilized by steam autoclaving, ethylene oxide, or ionizing radiation (i.e., Gamma Processing) in cases where the antibiotic in question was sensitive to extreme heat. Petri dishes containing the agar/antibiotic mixture were poured and the prospective microorganisms (selected from a single colonies) were streaked on these plates.

Surviving (i.e., viable) bacterial colonies were then selected and transferred to new antibiotic-containing media in which the concentration of the selected antibiotic was gradually increased to therapeutic levels. At each stage of the selection process, surviving colonies of *Bacillus coagulans* were selected and transferred to new media until therapeutic level antibiotic resistance is established.

7. Probiotic Activity of Bacillus Coagulans

It is well-documented clinically that many species of bacterial, mycotic and yeast pathogens possess the ability to cause a variety of gastrointestinal disorders including, but not limited to: disruption of normal gastrointestinal biochemical function, necrosis of gastrointestinal tissues, and disruption of the bioabsorption of nutrients, and like conditions. Therefore, the utilization of the probiotic microorganism-containing compositions of the present invention inhibits these pathogens are useful in the prophylactic or therapeutic treatment of conditions associated with infection by these aforementioned pathogens.

7.1 Anti-Microbial Probiotic Activity

The ability of *Bacillus coagulans* to inhibit various bacterial pathogens was quantitatively ascertained by use of an in vitro assay. This assay is part of a standardized bacterial pathogen screen (developed by the U.S. Food and Drug Administration(FDA)) and is commercially available on solid support disks (DIFCO® BACTROL® Antibiotic Disks). To perform the assay, potato-dextrose plates (DIFCO®) were initially prepared using standard procedures. The plates were then individually inoculated with the bacteria (approximately $1.5 \times 10^6$ CFU) to be tested so as to form a confluent bacterial bed.

Inhibition by *Bacillus coagulans* was subsequently ascertained by placing approximately $1.8 \times 10^6$ CFU of *Bacillus coagulans* in 10 µl of broth or buffer, directly in the center of the potato-dextrose plate with one test locus being approximately 8 mm in diameter per plate. A minimum of three test loci were used for each assay. The negative control consisted of a 10 µl volume of a sterile saline solution, whereas the positive control consisted of a 1 µl volume of glutaraldehyde. The plates were then incubated for approximately about 18 hr at 30° C., at which time the zones of inhibition were measured. As designated herein, "excellent inhibition" means the zone was 10 mm or greater in diameter; and "good inhibition" means the zone was greater than 2 mm in diameter but less than 10 mm in diameter.

As expected, no "inhibition" was seen with the negative, saline control, and excellent "inhibition" (approximately 16.2 mm diameter; average of three tests) was seen with the positive, glutaraldehyde control. For the enteric microorganisms tested, the following inhibition by *Bacillus coagulans* was found: (i) *Clostridium* species—excellent inhibition; (ii) *Escherichia coli*—excellent inhibition; (iii) *Clostridium* species—excellent inhibition, where the zone of inhibition was consistently greater than 15 mm in diameter. Similarly, excellent inhibition was also seen for the opportunistic pathogens *Pseudornonas aeruginosa*, and *Staphylococcus aureus*. In summation, pathogenic enteric bacteria which were shown to be inhibited by *Bacillus coagulans* activity include, but are not limited to: *Staphylococcus aureus; Staphylococcus epidermidis; Streptococcus pyogenes; Pseudomonas aeruginosa; Escherichia coli*(enterohemorragic species); numerous *Clostridium* species (e.g., *Clostridium perfingens, Clostridium botulinum, Clostridium tributrycum, Clostridium sporogenes*, and the like); *Gardnereia vaginails; Proponbacterium aenes; Aeromonas hydrophia; Aspergillus species; Proteus species*; and *Klebsiella* species.

7.2 Anti-Mycotic Probiotic Activity

The ability of *Bacillus coagulans* to inhibit various fungal pathogens was demonstrated using an in vitro assay. The tested fungal strains of *Trichophyton* species are available from the American Type Culture Collection (ATCC; Rockville, Md.) and their ATCC accession numbers are illustrated in FIG. 2.

In the assay, potato-dextrose plates (DIFCO®, Detroit, Mich.) were prepared using standard procedures and were inoculated individually with a confluent bed (about $1.7 \times 10^6$) of various species of the fungus *Trichophyton*. Inhibition by *Bacillus coagulans* was ascertained by placing on the plate approximately $1.5 \times 10^6$ colony forming units (CFU) in 10 μl of broth or buffer, plated directly in the center of the potato-dextrose plate, with one test locus per plate. The size of each test locus was approximately 8 mm in diameter and a minimum of three tests were performed for each inhibition assay. The negative control consisted of a 10 ml volume of sterile saline solution, whereas the positive control consisted of a 10 ml volume 2% Miconazole (1-[2-(2,4-dichlorophenyl)-2-[(2, 4-dichlorophenyl)methoxylmethyl-1,11-imidazole within an inert cream.

The plates were then incubated for approximately 18 hr at 30° C., at which time the zones of inhibition were measured. As designated herein, "excellent inhibition" means the zone was 10 mm or greater in diameter; and "good inhibition" means the zone was greater than 2 mm in diameter, but less than 10 mm in diameter.

The results of in vitro inhibition by *Bacillus coagulans* are illustrated in FIG. 2. For each of the *Trichophyton* species tested, the disease condition associated with an infection is indicated in column 2 of FIG. 2. For comparison, no zone of inhibition was seen with the negative control, whereas good inhibition (approximately 8.5 mm diameter, mean average of three tests) was seen with the positive control.

7.3 Probiotic Inhibition of Yeast

Similarly, the ability of *Bacillus coagulans* to inhibit various yeast pathogens was demonstrated in vitro for four species of *Candida*, all of which are available from the American Type Culture Collection (ATCC; Rockville, Md.) with their ATCC accession numbers illustrated in FIG. 3.

In the assay, potato-dextrose plates (DIFCO®, Detroit, Mich.) were prepared using standard procedures and were inoculated individually with a confluent bed about $1.7 \times 10^6$ of the four species of *Candida*. Inhibition by B. coagulans was tested by placing on the plate about $1.5 \times 10^6$ colony forming units (CFU) in 10 μl of broth or buffer, plated directly in the center of the potato-dextrose plate with one test locus of about 8 mm in diameter per plate. A minimum of three tests were performed for each inhibition assay. The negative control consisted of a 1 ml volume of a sterile saline solution, whereas the positive control consisted of a 1 ml volume of Miconazole cream.

The plates were then incubated for approximately 18 hr at 30° C., at which time the zones of inhibition were measured. As designated herein, "excellent inhibition" means the zone was 10 mm or greater in diameter; and "good inhibition" means the zone was greater than 2 mm in diameter, but less than 10 mm in diameter.

The results of the in vitro tests are shown in FIG. 3 with the pathological conditions in humans associated with infection by the *Candida* species shown in column 2. As expected, no inhibition was seen with the negative control and good inhibition (approximately 8.7 mm diameter; average of three tests) was seen with the positive control.

8. Therapeutic Compositions 8.1 Anti-Microbial Agent-Containing Therapeutic Compounds It should be noted that although *Bacillus coagulans* is utilized herein as a preferred exemplary probiotic species, by virtue of the common physiological characteristics which are indigenous to all lactic acid-producing bacteria, other species of these lactic acid-producing bacteria may be effectively in the methods and/or therapeutic compositions disclosed in the present invention. Preferred, exemplary formulations of the therapeutic compositions of the present invention are set forth in FIG. 4.

The cells/spores can be presented in a variety of compositions suited for oral administration to the gastrointestinal tract, directed at the objective of introducing the bacteria to tissues of the gastrointestinal tract. Therapeutic compositions of the present invention are, for example, comprised of a lactic acid-producing bacteria strain, preferably vegetative *Bacillus coagulans, Bacillus coagulans* spores, or combinations thereof which are a co-administrated with a selected agents which possesses the ability to ameliorate infections which have a bacterial, fungal, and/or yeast etiology. In the aforementioned embodiment, the active lactic acid-producing bacteria species of the present invention comprise approximately 0.1% to 50% by weight of the final composition and, preferably, approximately 1% to 10% by weight, contained within a formulation suitable for oral administration. More specifically, the therapeutic composition of the present invention may contain, within a 350 mg dosage formulation, for example, approximately $2 \times 10^6$ to $1 \times 10^{10}$ colony forming units (CFU) of viable, lactic acid-producing vegetative bacteria or bacterial spores (in the case of *Bacillus coagulans*).

The formulation for a therapeutic composition of the present invention may also include other probiotic agents or nutrients which promote spore germination and/or bacterial growth. A particularly preferred material is a bifidogenic oligosaccharide, which promotes the growth of beneficial probiotic bacteria as previously described, supra. Bifidogenic oligosaccharides (e.g., fructo-oligosaccharide (FOS) or gluco-oligosaccharide (GOS)) may be utilized in various combinations, depending upon the specific formulation. The preferred therapeutic composition includes approximately 10 to 200 mg of bifidogenic oligosaccharide, and most preferably a concentration of approximately 100 to 500 mg of bifidogenic oligosaccharide per unit of the therapeutic composition. Additionally, the therapeutic composition of the present invention may include other probiotic agents or nutrients for promoting growth, as well as other physiologically-active constituents which do not interfere with the overall therapeutic efficacy of the other active agents contained within the therapeutic composition.

In another embodiment of the present invention, the *Bacillus coagulans* strain is combined with a therapeutically-effective dose of an (preferably, broad-spectrum) antibiotic. The therapeutic composition of the present invention may also contain approximately 1 to approximately 250 mg of the selected antibiotic per unit of therapeutic composition. In preferred embodiments of the present invention, the *Bacillus coagulans* strain is combined with a therapeutic dose of an antibiotic such as Gentamicin; Vancomycin; Oxacillin; Tetracyclines; Nitroflurantoin; Chloramphenicol; Clindamycin; Trimethoprim-Sulfamethoxasole; a member of the Cephlosporin antibiotic family (e.g., Cefaclor, Cefadroxil, Cefixime, Cefprozil, Ceftriaxone, Cefuroxime, Cephalexin, Loracarbef, and the like); a member of the Penicillin family of antibiotics (e.g., Ampicillin, Amoxicillin/Clavulanate, Bacampicillin, Cloxicillin, Penicillin VK, and the like); with a member of the Fluoroquinolone family of antibiotics (e.g., Ciprofloxacin, Grepafloxacin, Levofloxacin, Lomefloxacin, Norfloxacin, Ofloxacin, Sparfloxacin, Trovafloxacin, and the like); or a member of the Macrolide antibiotic family (e.g., Azithromycin, Erythromycin, and the like).

In another embodiment of the present invention, the *Bacillus coagulans* strain is combined with a therapeutically-effective dose of an anti-fungal agent. The therapeutic composition of the present invention may also contain approximately 1 to 250 mg of the selected anti-fungal agent per unit of therapeutic composition. Typical anti-fungal agents which may be utilized include, but are not limited to: Clotrimazole, Fluconazole, Itraconazole, Ketoconazole, Miconazole, Nystatin, Terbinafine, Terconazole, Tioconazole, and the like.

In a preferred embodiment, *Bacillus coagulans* spores, a therapeutically-effective concentration of an antibiotic, anti-fungal, etc., and, if so desired, various other components (e.g., bifidogenic oligosaccharide, binders, etc.) are encapsulated into an enterically-coated, time-released capsule or tablet. The enteric coating allows the capsule/tablet to remain intact undissolved) as it passes through the gastrointestinal tract, until such time as it reaches the small intestine. Similarly, the time-released component prevents the "release" of the *Bacillus coagulans* spores for a pre-determined time period which, preferably, will coincide with the end of the antibiotic treatment period as the antibiotic prevents the spores from germinating until such time as the serum levels drop to a substantially low level. Once the antibiotic regimen is completed, the *Bacillus coagulans* spores germinate and this microorganism becomes the primary resident flora of the gastrointestinal tract, due to the killing-off of the previous resident flora by the antibiotic.

In addition, the vegetative *Bacillus coagulans* microorganisms do not adhere to the intestinal epithelium. Thus (without a repeat dosage), the bacteria remain in the gastrointestinal tract for maximal time of approximately 10 days and are considered to be a transient flora. The relatively rapid gastrointestinal-clearance time and inability to adhere to the gastrointestinal epithelium of *Bacillus coagulans*, has the advantage of preventing the later development of bacteremia in (for example) immunocompromised individuals.

The therapeutic compositions of the present invention may also include known antioxidants, buffering agents, and other agents such as coloring agents, flavorings, vitamins or minerals. For example, a preferred therapeutic composition may also contain one or more of the following minerals: calcium citrate (15-350 mg); potassium gluconate (5-150 mg); magnesium citrate (5-15 mg); and chromium picollinate (5-200 µg). In addition, a variety of salts may be utilized, including calcium citrate, potassium gluconate, magnesium citrate and chromium picollinate. Thickening agents may be added to the compositions such as polyvinylpyrrolidone, polyethylene glycol or carboxymethylcellulose. Preferred additional components of a therapeutic composition of this invention can include assorted colorings or flavorings, vitamins, fiber, enzymes and other nutrients. Preferred sources of fiber include any of a variety of sources of fiber including, but not limited to: psyllium, rice bran, oat bran, corn bran, wheat bran, fruit fiber and the like. Dietary or supplementary enzymes such as lactase, amylase, glucanase, catalase, and the like enzymes can also be included. Chemicals used in the present compositions can be obtained from a variety of commercial sources, including Spectrum Quality Products, Inc (Gardena, Calif.), Sigma Chemicals (St. Louis, Mich.), Seltzer Chemicals, Inc., (Carlsbad, Calif.) and Jarchem Industries, Inc., (Newark, N.J.).

The various active agents (e.g., probiotic bacteria, antibiotics, anti-fungal agents, bifidogenic oligosaccharides, and the like) are combined with a carrier which is physiologically compatible with the gastrointestinal tissue of the species to which it is administered. Carriers can be comprised of solid-based, dry materials for formulation into tablet, capsule or powdered form; or the carrier can be comprised of liquid or gel-based materials for formulations into liquid or gel forms. The specific type of carrier, as well as the final formulation depends, in part, upon the selected route(s) of administration.

The therapeutic composition of the present invention may also include a variety of carriers and/or binders. A preferred carrier is micro-crystalline cellulose (MCC) added in an amount sufficient to complete the one gram dosage total weight. Particularly preferred formulations for a therapeutic composition of this invention will be described, infra. Carriers can be solid-based dry materials for formulations in tablet, capsule or powdered form, and can be liquid or gel-based materials for formulations in liquid or gel forms, which forms depend, in part, upon the routes of administration.

Typical carriers for dry formulations include, but are not limited to: trehalose, malto-dextrin, rice flour, micro-crystalline cellulose (MCC) magnesium sterate, inositol, FOS, GOS, dextrose, sucrose, and like carriers. Where the composition is dry and includes evaporated oils that produce a tendency for the composition to cake (adherence of the component spores, salts, powders and oils), it is preferred to include dry fillers which distribute the components and prevent caking. Exemplary anti-caking agents include MCC, talc, diatomaceous earth, amorphous silica and the like, and are typically added in an amount of from approximately 1% to 95% by weight. It should also be noted that dry formulations which are subsequently rehydrated (e.g., liquid formula) or given in the dry state (e.g., chewable wafers, pellets or tablets) are preferred to initially hydrated formulations. Dry formulations (e.g., powders) may be added to supplement commercially available foods (e.g., liquid formulas, strained foods, or drinking water supplies). Similarly, the specific type of formulation depends upon the route of administration.

Suitable liquid or gel-based carriers include but are not limited to: water and physiological salt solutions; urea; alcohols and derivatives (e.g., methanol, ethanol, propanol, butanol); glycols (e.g., ethylene glycol, propylene glycol, and the like). Preferably, water-based carriers possess a neutral pH value (i.e., pH 7.0). The compositions may also include natural or synthetic flavorings and food-quality coloring agents, all of which must be compatible with maintaining viability of the lactic acid-producing microorganism. Well-known thickening agents may also be added to the compositions such as corn starch, guar gum, xanthan gum, and the like. Where a liquid-based composition containing spores is provided, it is desirable to include a spore germination inhibitor to promote long term storage. Any spore germination inhibitor may be used. By way of example and not of limitation, preferred inhibitors include: hyper-saline carriers, methylparaben, guargum, polysorbates, preservatives, and the like.

Preservatives may also be included within the carrier including methylparaben, propylparaben, benzyl alcohol and ethylene diamine tetraacetate salts. Well-known flavorings and/or colorants may also be included within the carrier. The compositions of the present invention may also include a plasticizer such as glycerol or polyethylene glycol (with a preferred molecular weight of MW=800 to 20,000). The composition of the carrier can be varied so long as it does not interfere significantly with the pharmacological activity of the active ingredients or the viability of the Bacillus coagulans spores.

A composition can be formulated to be suitable for oral administration in a variety of ways, for example in a liquid, a powdered food supplement, a paste, a gel, a solid food, a packaged food, a wafer, and the like. Other formulations will be readily apparent to one skilled in the art.

A nutrient supplement component of a composition of this invention can include any of a variety of nutritional agents, as are well known, including vitamins, minerals, essential and non-essential amino acids, carbohydrates, lipids, foodstuffs, dietary supplements, and the like. Preferred compositions comprise vitamins and/or minerals in any combination. Vitamins for use in a composition of this invention can include vitamins B, C, D, E, folic acid, K, niacin, and like vitamins. The composition can contain any or a variety of vitamins as may be deemed useful for a particularly application, and therefore, the vitamin content is not to be construed as limiting. Typical vitamins are those, for example, recommended for daily consumption and in the recommended daily amount (RDA), although precise amounts can vary. The composition would preferably include a complex of the RDA vitamins, minerals and trace minerals as well as those nutrients that have no established RDA, but have a beneficial role in healthy human or mammal physiology. The preferred mineral format would include those that are in either the gluconate or citrate form because these forms are more readily metabolized by lactic acid bacteria. In a related embodiment, the invention contemplates a composition comprising a viable lactic acid bacteria in combination with any material to be adsorbed, including but not limited to nutrient supplements, foodstuffs, vitamins, minerals, medicines, therapeutic compositions, antibiotics, hormones, steroids, and the like compounds where it is desirable to insure efficient and healthy absorption of materials from the gastrointestinal track into the blood. The amount of material included in the composition can vary widely depending upon the material and the intended purpose for its absorption, such that the invention is not to be considered as limiting. Other components of the compositions of the present invention can be a bifidogenic oligosaccharide, as described herein.

By way of example, and not of limitation, Bacillus coagulans spores may be incorporated into any type of dry or lyophilized product which is dissolved or mixed with hot water, so long as the temperature of the Bacillus coagulans spore-containing mixture is raised to the required heat-shock temperature (i.e., 80° C. for 5 minutes) necessary for germination of the spores. The Bacillus coagulans spores may either be incorporated into the dry or lyophilized product by the manufacturer of the product or by the consumer during preparation. These dry or lyophilized product include, but are not limited to: tea bags, coffee (e.g., "freeze-dried" or ground), sweeteners (e.g., synthetic (NutraSweet®) and natural); hot cereal (e.g., oatmeal, Cream of Wheat®, and the like), hot beverage condiments/flavorings and creamers, and the like.

In another specific embodiment, Bacillus coagulans spores may be utilized as a dry or lyophilized product, or incorporated into a chewable tablet, toothpaste, mouthwash, oral drops, and the like in order to inhibit the formation of dental caries, gingivitis, and other forms of periodontal disease. Similarly, Bacillus coagulans spores may be incorporated, with or without anti-microbial agents, chewable tablet, toothpaste, mouthwash, oral drops, and the like in order to treat oral infections caused by yeast (i.e., "thrush"), Herpes simplex I (i.e., cold sores), and various other infections caused by oral pathogens.

In yet another specific embodiment, the Bacillus coagulans vegetative bacterial cells/spores may incorporated into an aqueous solution (e.g., physiological saline) for administration as a colonic, via an enema or the like) so as to directly administer the probiotic bacteria to the colon. This method of administration is highly efficacious for utilization of vegetative bacterial cells as they are not exposed to the highly acidic environment of the stomach as is the case during oral administration.

8.2 Therapeutic Compositions Methods for Treating Bacterial Infections

The present invention contemplates a method for treating, reducing or controlling gastrointestinal bacterial infections using the therapeutic composition or therapeutic system disclosed herein. The disclosed methods of treatment function so as to inhibit the growth of the pathogenic bacteria which are associated with gastrointestinal infections, as well as to concomitantly mitigate the deleterious physiological effects/symptoms of these pathogenic infections.

Probiotic lactic acid bacterium, preferably Bacillus coagulans, are generally regarded as safe by those skilled within the art (i.e., GRAS Certified by the FDA) and, therefore, suitable for direct ingestion in food stuffs or as a food supplement. The methods of the present invention comprise administration of a therapeutic composition containing a viable lactic acid-producing bacteria to the gastrointestinal tract of a human or animal, to treat or prevent bacterial infection. Administration is preferably made using a liquid, powder, solid food and the like formulation compatible with oral administration, all formulated to contain a therapeutic composition of the present invention by use of methods well-known within the art.

The methods of the present invention includes administration of a composition containing lactic acid-producing bacterial cells (i.e., vegetative bacterial cells) and/or spores or isolated Bacillus coagulans extracellular products (which contains a metabolite possessing antibiotic-like properties) to a human or animal, so as to treat or prevent the colonization of antibiotic-resistant pathogens with the gastrointestinal tract. In particular, for VRE, VISA, PRP, and other pathogens, the methods includes administering to the patient, for example, Bacillus coagulans in food or as a food supplement. Oral administration is preferably in an aqueous suspension, emulsion, powder or solid, either already formulated into a food, or as a composition which is added to food by the user prior to consumption. Administration to the gastrointestinal tract may also be in the form of an anal suppository (e.g., in a gel or semi-solid formulation). All such formulations are made using standard methodologies.

Administration of a therapeutic composition is preferably to the gastrointestinal tract using a gel, suspension, aerosol spray, capsule, tablet, powder or semi-solid formulation (e.g., a suppository) containing a therapeutic composition of the present invention, all formulated using methods well-known within the art. Administration of the compositions containing the active probiotic lactic acid-producing bacterium which is effective in preventing or treating a pathogenic bacterial infection, generally consist of one to ten dosages of approximately 10 mg to 10 g of the therapeutic composition per dosage, for a time period ranging from one day to one month. Administrations are (generally) once every twelve hours and up to once every four hours. In the preferred embodiment, two to four administrations of the therapeutic composition per day, of approximately 0.1 g to 5 g per dose, for one to seven days. This preferred dose is sufficient to prevent or treat a pathogenic bacterial infection. Of course, the specific route, dosage and timing of the administration will depend, in part, upon the particular pathogen and/or condition being treated, as well as the extent of said condition.

A preferred embodiment of the present invention involves the administration of from approximately $1 \times 10^3$ to $1 \times 10^{14}$ CFU of viable, vegetative bacteria or spore per day, more preferably from approximately $1 \times 10^5$ to $1 \times 10^{10}$, and most preferably from approximately $5 \times 10^8$ to $1 \times 10^9$ CFU of viable, vegetative bacteria or spores per day. Where the condition to be treated involves antibiotic-resistant digestive pathogens and the patient is an adult, the typical dosage is approximately $1 \times 10^2$ to $1 \times 10^{14}$ CFU of viable, vegetative bacteria or spores per day, preferably from approximately $1 \times 10^8$ to $1 \times 10^{10}$, and more preferably from approximately $2.5 \times 10^8$ to $1 \times 10^{10}$ CFU of viable, vegetative bacteria or spores per day. Where the condition to be treated is Sudden Infant Death Syndrome (SIDS) and the patient is an infant over 6 months old, the dosage is typically $1 \times 10^6$ to $1 \times 10^9$, preferably from approximately $5 \times 10^4$ to $2.5 \times 10^5$, and more preferably from approximately $1.5 \times 10^5$ to $2 \times 10^5$ CFU of viable, vegetative bacteria or spores per day.

In addition, the present invention contemplates a method which comprises oral administration of a composition that contains from approximately 10 mg to 20 g of a bifidogenic oligosaccharide, preferably a fructo-oligosaccharide (FOS), per day, preferably from approximately 50 mg to 10 g, and more preferably from approximately 150 mg to 5 g per day, to preferentially promote the growth of the probiotic lactic acid-producing bacterium over the growth of the pathogen. The method can be combined with treatment methods using a probiotic lactic acid-producing bacterium as described herein.

The present invention further contemplates a therapeutic system for treating, reducing and/or controlling pathogenic bacterial infections. Typically, the system is in the form of a package containing a therapeutic composition of the present invention, or in combination with packaging material. The packaging material includes a label or instructions for use of the components of the package. The instructions indicate the contemplated use of the packaged component as described herein for the methods or compositions of the invention.

By way of example, and not of limitation, a system can comprise one or more unit dosages of a therapeutic composition according to the present invention. Alternatively, the system can alternately contain bulk quantities of a therapeutic composition. The label contains instructions for using the therapeutic composition in either unit dose or in bulk forms as appropriate, and may also include information regarding storage of the composition, disease indications, dosages, routes and modes of administration and the like information.

Furthermore, depending upon the particular contemplated use, the system may optionally contain either combined or in separate packages one or more of the following components: bifidogenic oligosaccharides, flavorings, carriers, and the like components. One particularly preferred embodiment comprises unit dose packages of *Bacillus* spores for use in combination with a conventional liquid product, together with instructions for combining the probiotic with the formula for use in a therapeutic method.

9. Utilization of the Therapeutic Compositions of the Present Invention in the Treatment of Bacterial Gastroenteritis Several microbial species have been quantitatively ascertained as the etiology for the vast majority of food-borne gastrointestinal infection (i.e., bacterial gastroenteritis), with *Campylobacter jejuni*-mediated campylobacteriosis being the most commonly reported (46%) cause of bacterial gastroenteritis in the United States, followed in prevalence by *Salmonella typhimurium*-mediated salmonellosis (28%); shigellosis (17%); and *Escherichia coli*0157 infection (5%). In addition, it is quite possible that various Salmonella and Shigella species may eventually acquire antibiotic resistance (i.e., Metacillin or Vancomycin) in that same manner in which *Enterococci* originally acquired antibiotic resistance from *Staphylococcus aureus*.

Although the methodologies disclosed in the present invention are equally applicable to the therapeutic intervention of all forms of bacterial gastroenteritis, by way of example and not of limitation, the following discussion will be primarily limited to the utilization of these methodologies in the treatment of *Campylobacter jejuni*-mediated bacterial gastroenteritis.

*Campylobacter jejuni* was first identified as a human gastrointestinal tract (i.e., diarrheal) pathogen in 1973. As previously stated, in 1996, 46% of all laboratory-confirmed cases of bacterial gastroenteritis reported to the Centers for Disease Control and Prevention (CDC) were caused by *Campylobacter* species. In the United States alone, an estimated 2.1 to 2.4 million cases of human campylobacteriosis occur each year. See e.g., Tauxe, R. V. Epidemiology of *Campylobacter jejuni* infections in the United States and other industrial nations. In: *Campylobacter jejuni: current and future trends*. P. 9-13 (Nachamkin, I. and Tompkins L. S., editors; American Society for Microbiology; 1992). Less frequently, *Campylobacter jejuni* infections have also been reported to cause bacteremia, septic arthritis, and various other extra-intestinal pathology. See e.g., Peterson, M. C., 1994. Wes. J. Med. 161: 148-152. In addition, an increasing proportion of human infections caused by *Campylobacter jejuni* are resistant to anti-microbial therapy. The mishandling of raw poultry and consumption of undercooked poultry are the major risk factors for human campylobacteriosis.

Deaths from *Campylobacter jejuni*-related infections are relatively rare, and occur primarily in infants, the elderly, and individuals with underlying illnesses. For example, the incidence of campylobacteriosis in HIV-positive/AIDS patients is markedly higher than in the general population. In Los Angeles County between 1983 and 1987, the reported incidence of campylobacteriosis in patients with AIDS was 519 cases per 100,000 population, which is 39-times higher than the rate in the general population. See e.g., Sorvillo, F. J. et al., 1991. *J. Acquired Immune Defic. Syndr. Hum. Retrovirol.* 4: 595-602. Common complications of campylobacteriosis in HIV-infected individuals include recurrent infections with antimicrobial-resistant bacterial strains. See e.g., Penman, D. J. et al., 1988. *Ann. Intern. Med.* 108: 540-546.

9.1 Pathophysiology of *Campylobacter Jejuni*-Mediated Gastroenteritis

The pathophysiology of Campylobacter jejuni-mediated gastroenteritis involves both host- and pathogen-specific factors. Factors including, but not limited to, the overall health and age of the host (see e.g., Tauxe, R. V. Epidemiology of *Campylobacter jejuni* infections in the United States and other industrial nations. In: *Campylobacter jejuni: current and future trends*. P. 9-13 (Nachamkin, I. and Tompkins L. S., editors; American Society for Microbiology; 1992) and *Campylobacter jejuni*-specific humoral immunity from previous exposure (see e.g., Blaser, M. J. et al., 1987. *JAMA* 257: 43-46) influence the clinical outcome following infection.

The ingestion of relatively low numbers of viable organisms is sufficient to cause infection in healthy adults. For example, in one volunteer study, *Campylobacter jejuni* infection was demonstrated to occur after the ingestion of as few as 800 organisms, with the overall rates of infection increasing as a function of the ingested dose. See e.g., Black, R. E. et al., 1988. *J. Infect. Dis.* 157: 472-479. In addition, the rates of infection appeared to increase when bacterial inocula were ingested in a suspension buffered to reduce gastric acidity. See e.g., Black, R. E. et al., 1988. *J. Infect. Dis.* 157: 472-479. Similarly, both rates of *Campylobacter jejuni* infectivity and the severity of accompanying disease appeared to be positively effected by disturbances in the overall gastrointestinal "health" of the infected individual (e.g., secondary disease or infection precipitating lowered levels of normal gastrointestinal flora, and the like. In accord, the sensitivity of *Campylobacter jejuni* to decreased pH (i.e., acidic environments) and competing bacterial species serves to illustrate the potential efficacy of the utilization of the antibiotic resistant, lactic acid-producing probiotic bacteria (in combination with the appropriate antibiotic) disclosed in the present invention to mitigate the in vivo growth of *Campylobacter jejuni*, and hence its rate of infectivity, by generating an inhospitable acidic, competitive environment within the individual's gastrointestinal tract.

Many pathogen-specific virulence determinants may contribute to the pathogenesis of *Campylobacter jejuni*-mediated infection, but none has a quantitatively ascertained role. See e.g., Ketley, J. M., 1997. *Microbiology* 143: 5-21. Suspected determinants of pathogenicity include, but are not limited to: chemotaxis, motility, and flagella, all of which are required for attachment and colonization of the gastrointestinal epithelium. See e.g., Ketley, J. M., 1997. *Microbiology* 143: 5-21. Once colonization occurs, other possible virulence determinants are iron acquisition, host cell invasion, toxin production, inflammation and active secretion, and epithelial disruption with leakage of serosal fluid. See e.g., Ketley, J. M., 1997. *Microbiology* 143: 5-21.

9.2 Sequelae to *Campylobacter jejuni* Infection

Several chronic, extra-gastrointestinal sequelae are associated with *Campylobacter jejuni*-mediated bacterial gastroenteritis (e.g., Guillain-Barré syndrome and Reiter syndrome—a reactive type of arthropathy).

Guillain-Barré syndrome (GBS), a demyelating disorder resulting in acute neuromuscular paralysis, is a serious sequelae of *Campylobacter* infection. See e.g., Allos, B. M., 1997. *J. Infect. Dis.* 176: 5125-5128. It has been estimated that one case of GBS occurs for every 1,000 cases of campylobacteriosis and up to 40% of patients with the syndrome have demonstrated evidence of recent Campylobacter infection. Approximately 20% of patients with GBS are left with some disability, and approximately 5% die despite recent advances in respiratory care.

Campylobacteriosis is also associated with Reiter syndrome, a reactive arthropathy. See e.g., Peterson, M. C., 1994. *Scand. J. Rheumatol.* 23: 167-170. In approximately 1% of patients with campylobacteriosis, the sterile post-infection process occurs 7 to 10 days after onset of diarrhea. Multiple joints can be affected, particularly the knee joint. Pain and incapacitation can last for months or, in some cases, become chronic.

Both GBS and Reiter syndrome are thought to be autoimmune responses stimulated by infection. For example, many individuals with Reiter syndrome have been found to carry the HLA B27 antigenic marker. See e.g., Peterson, M. C., 1994. *Scand. J. Rheumatol.* 23: 167-170. Unfortunately, the pathogenesis of GBS (see e.g., Shoenfeld, Y. et al., 1996. *Int. Arch. Allergy Immunol.* 109: 318-326) and Reiter syndrome is not completely understood.

9.3 Anti-Microbial-Resistant Strains of *Campylobacter Jejuni*

The increasing rate of human infections caused by anti-microbial-resistant strains of *Campylobacter jejuni* makes clinical management of cases of campylobacteriosis markedly more difficult. See e.g., Murphy, G. S. et al., 1996. *Clin. Infect. Dis.* 22: 568-569; Piddock, L. V., 1995. *Antimicrob. Agents Chemother.* 36: 891-898. As previously discussed, anti-microbial resistance can prolong illness and compromise treatment of patients with bacteremia. Interestingly, the rate of anti-microbial-resistant *Campylobacter jejuni*-mediated enteric infections is highest in the developing world, where the use of anti-microbial drugs in humans and animals is relatively unrestricted. For example, a 1994 study found that most clinical isolates of *Campylobacter jejuni* from United States troops in Thailand were demonstrated to be resistant to the broad spectrum antibiotic, Ciprofloxacin. Similarly, approximately one-third of *Campylobacter jejuni* isolates from United States troops located in Hat Yai were also found to be resistant to Azithromycin. See e.g., Murphy, G. S. et al., 1996. *Clin. Infect. Dis.* 22: 568-569.

In the industrialized world, the emergence of *Campylobacter jejuni* strains which have been found to be resistant to the broad spectrum antibiotic Fluoroquinolone, is illustrative of the need for prudent anti-microbial use in food-animal production. See e.g., Piddock, L. V., 1995. *Antimicrob. Agents Chemother.* 36: 891-898. Experimental evidence demonstrates that Fluoroquinolone-susceptible *Campylobacter jejuni* readily become drug-resistant in poultry when these drugs are administered. See e.g., Jacobs-Reitsma, W. F. et al., The induction of quinolone resistance in *Campylobacter* bacteria in broilers by quinolone treatment. In: *Campylobacter, Helicobacters, and related organisms*. 1996. (Newell, D. G., Ketley, J. M., and Feldman, R. A., editors. New York: Plenum Press) p. 307-11. After Fluoroquinolone use in poultry was approved in Europe, resistant *Campylobacter jejuni* strains were shown to rapidly emerge in humans during the early 1990's. See e.g., Piddock, L. V., 1995. *Antimicrob. Agents Chemother.* 36: 891-898. Similarly, within 2 years of the 1995 approval of Fluoroquinolone use for poultry in the United States, the number of domestically-acquired human cases of Ciprofloxacin-resistant campylobacteriosis doubled in Minnesota. In a 1997 study conducted in Minnesota, (20%) of 60 *Campylobacter jejuni* isolates obtained from chicken purchased in grocery stores were found to be Ciprofloxacin-resistant. See e.g., Smith, K. E. et al., Fluoroquinolone-resistant *Campylobacter* isolated from humans and poultry in Minnesota. 1995. Program of the 1st International Conference on Emerging Infectious Diseases; Mar 7-10, 1998. Centers for Disease Control and Prevention; Atlanta, Ga.

9.4 Treatment of *Campylobacter Jejuni*-Mediated Infections

Current, traditional therapeutic modalities primarily involve supportive measures, particularly fluid and electrolyte replacement, for most patients with campylobacteriosis. See e.g., Blaser, M. J., *Campylobacter* Species. In: *Principles and practice of infectious diseases.* 1990. p. 1649-1658 (Mandell, G. L., ed., Churchhill Livingstone). Severely dehydrated patients should receive rapid volume expansion with intravenous fluids, however for most other patients, oral rehydration is indicated.

Although *Campylobacter* infections are generally self-limiting in nature, antibiotic therapy may be prudent for patients who have high fever, bloody diarrhea, or more than eight stools in 24 hours; immunosuppressed patients, patients with systemic infections, and those whose symptoms worsen or persist for more than 1 week from the time of initial diagnosis. When indicated, anti-microbial therapy soon after the onset of symptoms can reduce the median duration of illness from approximately 10 days to 5 days. However, when such treatment is delayed (e.g., until *Campylobacter jejuni* infection is confirmed by a medical laboratory), antibiotic therapy may not be successful. Ease of administration, lack of serious toxicity, and high degree of efficacy make erythromycin the drug of choice for *Campylobacter jejuni* infection; however, other anti-microbial agents, particularly the quinolones and newer Macrolides (e.g., Azithromycin) may also utilized.

The utilization of antibiotic agents, which kill the "normal" microbial flora, frequently exacerbates the deleterious physiological effects (e.g., diarrhea, loss of the gastrointestinal mucosa, dehydration, and the like) in individuals with Campylobacterjejuni-mediated bacterial gastroenteritis. Accordingly, the concomitant administration of an antibiotic and an antibiotic resistant probiotic microorganisms of the present invention to these individuals may ameliorate these aforementioned deleterious physiological symptomology by re-establishing the gastrointestinal microbial flora which serves to both directly compete with the pathogenic bacteria for required growth moieties (e.g., lipids, carbohydrates, electrolytes, amino acids, and the like), as well as making the gastrointestinal environment inhospitable to the continued growth of the pathogenic bacteria by lowering the pH through the production of lactic acid.

9.5 Other Bacterial Gastrointestinal Pathogens

Various other gastrointestinal pathogens, some antibiotic resistant, have been recently reported. These pathogens are amenable for prevention or treatment with the present invention.

For example, the FDA is investigating whether bacteria resistant to quinolone antibiotics can emerge in food animals and cause disease in humans. Although thorough cooking has been demonstrated to sharply reduce the likelihood of antibiotic-resistant bacteria surviving in meat infect a human, pathogens resistant to drugs other than fluoroquinolones have been sporadically reported to survive in meat and subsequently infect a human. In 1983, for example, 18 people in four midwestern states developed multi-drug-resistant Salmonella food poisoning after eating beef from cows fed antibiotics. Eleven of the people were hospitalized, and one died.

A study conducted by Cometta, et al., showed that increase in antibiotic resistance parallels increase in antibiotic use in humans. See e.g., Cometta, et al., 1994. *New Engl. J. Med.* 126: 43-47. They examined a large group of cancer patients given fluoroquinolone antibiotics. The patients' white blood cell counts were very low as a result of their cancer treatment, thus leaving them open to opportunistic infection. Between 1983 and 1993, the percentage of such patients receiving antibiotics rose from 1.4 to 45. During those years, the researchers isolated *Escherichia coli* bacteria annually from the patients, and tested the microbes for resistance to five types of fluoroquinolones. Between 1983 and 1990, all 92 E. coli strains tested were easily killed by the antibiotics. But from 1991 to 1993, 11 of 40 tested strains (28 percent) were found to be resistant to all five drugs.

10. Therapeutic Methods for Inhibiting Parasites in Animals

The present invention is also directed at methods for inhibiting growth of parasites and/or pathogenic organisms in the gastrointestinal tract of animals. The method comprises administering a composition of the present invention to the gastrointestinal tract of the animal, and thereby contact any parasites therein with an effective amount of the active ingredients in the composition.

As used herein, the terms "pathogen" and "parasite" are used interchangeably in the context of a deleterious organism growing in the gastrointestinal tract and/or feces of an animal, although it appreciated that these terms have distinctive meanings.

The present invention describes methods for inhibiting growth of a parasite in the gastrointestinal tract of an animal comprising the step of administering a composition of the invention to the gastrointestinal tract of the animal. A composition preferably contains diatomaceous earth and viable lactic acid-producing bacteria. The metabolic effect of diatomaceous earth present in a composition of this invention on parasites is to rupture tissues of the parasite, typically the soft cuticle portions of the ectoskeleton, based on the abrasive quality of the diatomaceous earth upon cuticles arising during the mechanical effects of movement of the parasite after contacting the CE. These ruptures in the cuticle breach the protective ectoskeleton of the parasite, rendering the parasite susceptible to infection, to dehydration, to fluid exchanges and/or fluid losses, and the like effects which inhibit parasite health, and thereby inhibit growth.

The combined use of diatomaceous earth with an lactic acid-producing bacteria provides an beneficial synergy which provides important benefits to the claimed compositions, methods and systems. As described herein, the use of the probiotic bacterial promotes healthy growth in the intestinal tract, competing out deleterious bacteria, making the tissues targeted by the deleterious bacteria more healthy. Parasites cause local tissue damage at the site of growth and feeding, and often provide inflammation and tissue injuries at the site as well. This tissue damage provides a pathogenic or unhealthy environment where the tissue is ruptured and/or compromised in health, allowing undesirable or opportunistic pathogens to grow in the tissue vicinity. Because the parasite damages tissue and creates an environment that favors pathogenic infections, diatomaceous earth inhibits both the parasite and the pathogenic infection by reducing the degree of tissue damage. Because the health of the host contributes to the ability to fight off the parasite, improvements in tissue health by decreasing pathogenic infections with probiotics increase the ability to inhibit parasite growth. Thus, the probiotic and the diatomaceous earth cooperate at inhibiting pathogens and parasites, respectively, which growth in turn promotes growth of each other, decreasing tissue damage and increasing digestive health of the host.

In one embodiment the invention contemplates methods for inhibiting growth of parasites and pathogenic organisms in the feces of animals. The method comprises administering a composition of the present invention into the gastrointestinal tract of an animal, thereby introducing the active ingredients of the composition into the intestinal tract of the animal. A composition containing diatomaceous earth in an effective amount controls and/or inhibits parasite or pathogen growth in feces by first interfering with viable growth in the intestines, where the parasite first grows, thereby reducing the amount of parasite arriving in (i.e., "inoculating") the feces, and subsequently by interfering with growth that occurs in the feces after the feces is deposited.

Insofar as feces provide growth and breeding grounds for undesirable organisms, controlling and/or inhibiting growth of parasites and pathogenic organisms in feces inhibits growth and reproduction of these undesirable organisms in areas where feces is produced, deposited and/or stored. For example, in barns or corrals, in animal cages, in feed lots, in zoological display enclosures, and the like areas where animals are maintained and feces is deposited, there is an opportunity for parasites/pathogens to irritate, spread, reproduce and/or infect other hosts. These circumstances provide a variety of undesirable problems solved by the present invention. For example, it is undesirable for parasites or pathogens to spread and further infect hosts, and thereof or any means to control spread of infection is of great benefit where multiple animals are caged together. In addition, in many circumstances biting of host animals by parasites or flying insects irritates and/or upsets animals, providing behavior problems which includes excessive kicking, biting and related activities which are unsafe for neighboring animals and for animal handlers.

In a particularly preferred embodiment, the invention contemplates a method for reducing and/or controlling flying insect populations in animal cages/pens/enclosures where animals are maintained comprising administering a composition of the present invention to the gastrointestinal tract of the caged animals.

The present invention is useful at controlling a large variety of parasites and pathogenic organisms, and therefore the invention need not be limited to inhibiting any particular genus or species of organism. For example, based on the mechanisms described herein for effectiveness of the composition, it is seen that all insect varieties which can act as an animal parasite can be targeted by the methods of the present invention. Parasites can infect any of a variety of animals, including mammals, reptiles, birds and the like, and therefore the invention is deemed to not be limited to any particular animal. Examples of well-known or important parasites are described herein for illustration of the invention, but are not to be viewed as limiting the invention. Representative parasites and animal and/or human hosts are described in extensive detail in a variety of veterinary treatises such as "Merck's Veterinary Manual" and "Cecils' Human Diseases" Parasites of horses includes horse bots, lip bots or throat bots, caused by *Gasterophilus* species, such as *G. intestinalis, G. haemorrhiodalis*, and *G. nasalis*, stomach worms, caused by *Habronema* species, such as *H. muscae* or *H. microstoma mulus*, or caused by *Crascia* species, such as *C. mepastoma*, or caused by *Trichostrongvlus* species, such as *T. axei*, ascarids (white worms) caused by *Parascaris* species such as *P. eciuorum*, blood worms (palisade worms, red worms or sclerostomes) caused by Stroncrvlus species such as *S. vulcraris, S. epuinus* or *S. edentatus*, small strongyles of the cecum and colon caused by *Triodontophorus* species such as *T. tenuicollis*, pinworms caused by *Oxvuris* species such as *O. eaui*, strongyloides infections of the intestine caused by *Stronciv-loides westeri*, tapeworms caused by *Anonlocephala* species such as *A. macma* and *A. perfoliata*, and caused by *Paranonlocephala mamillana*.

Various other parasites cause disease in ruminants, typically cattle, include the wire worm (or barber's pole worm or large stomach worm) caused by *Haemonchus* species. Parasites caused in ruminants, typically swine, include stomach worms caused by *Hvostroncmulus* species.

Additional parasites are known to infect a variety of animal hosts, and therefore are a target for treatment by the methods of the present invention. For example, gastrointestinal parasites infect a variety of animals and can include *Spirocerca* species such as *S. lupi* that cause esopheageal worms in canines and *Physoloptera* species that cause stomach worms in canines and felines.

In humans, a large variety of parasites are particularly important targets for the methods of the present invention insofar as these parasites are well known. However, the invention is not to be construed as limited to these parasites.

Where the animal is fed a pelletized or granular food, the composition can be included in the pelletized or granular food, or can comprise a mixture of the pelletized food combined with a pelletized composition of this invention. Mixing pelletized food with a pelletized formulation of a composition of this invention is a particularly preferred method for practicing the present invention, insofar as it provides a convenient system for using commercial feeds and simultaneously regulating the amounts of a composition of this invention to be administered.

Administration of a therapeutic composition is preferably to the gut using a gel, suspension, aerosol spray, capsule, tablet, granule, pellet, wafer, powder or semi-solid formulation (e.g., a suppository) containing a nutritional composition of this invention, all formulated using methods well known in the art.

The method comprises administration of a composition of this invention containing the active ingredients to a human or animal in various dosage regimens as described herein to achieve the nutritional result. Administration of the compositions containing the active ingredients effective in inhibiting parasite growth in the intestine and in feces generally consist of one to ten unit dosages of 10 mg to 10 g per dosage of the composition for one day up to one month for an animal of approximately 100 kg body weight. Unit dosages are generally given once every twelve hours and up to once every four hours. Preferably two to four dosages of the composition per day, each comprising about 0.1 g to 50 g per dosage, for one to seven days are sufficient to achieve the desired result.

A preferred method involves the administration into the digestive tract of from $1 \times 10^2$ to $1 \times 10^{10}$ viable bacterium or spore per day, in some embodiments from $1 \times 10^3$ to $1 \times 10^6$, in other embodiments from $1 \times 10^6$ to $1 \times 10^9$, and more preferably about from $5 \times 10^8$ to $1 \times 10^9$ viable bacterium or spore per day. Exemplary dosages range from about $1 \times 10^3$ to $1 \times 10^6$ viable bacterium per day, or alternatively range from about $1 \times 10^6$ to $1 \times 10^9$ viable bacterium per day.

In a related embodiment, a preferred method comprises administration of the composition which delivers from about 0.1 to 25% weight of diatomaceous earth per volume (w/v) of composition, where the composition is typically formulated as an animal feed, preferably about 0.5 to 10% (w/v), and more preferably about 1 to 5% (w/v). Typically, when used in animal feed a single dose route of administration will use a higher diatomaceous earth concentration, such as about 2 to 10% w/v, preferably about 5% w/v. When an animal feed route of administration is used in a daily feed mode, a lower diatomaceous earth concentration is typically used, for example about 0.5 to 2% w/v, preferably about 1% w/v. Stated differently, a typical unit dosage is a composition containing about 50 milligrams (mg) to 10 grams of diatomaceous earth, preferably from about 200 to 500 mg, per 100 kilogram animal per day.

In addition, a preferred method comprises administering into the digestive tract from 10 mg to 20 grams of fructo-oligosaccharide per day, preferably about 50 mg to 10 grams, and more preferably about from 150 mg to 5 grams of fructo-oligosaccharide per day. These dosages are expressed for an animal of approximately 70-100 kilogram body weight. For animals of other body sizes, the dosages are adjusted according to the above body weight to dosage ratios.

The method is typically practiced on any animal where inhibiting pathogen or parasites is desired. The animal can be any livestock or zoological specimen where such inhibition of parasites/pathogens provides economic and health benefits. Any animal can benefit by the claimed methods, including birds, reptiles, mammals such as horses, cows, sheep, goats, pigs, and the like domesticated animals, or any of a variety of animals of zoological interest. Other purposes are readily apparent to one skilled in the arts of nutrient absorption, feed utilization and bioavailability.

10.1. Therapeutic Systems for Inhibiting Parasite Growth

The present invention further contemplates a system for inhibiting growth of parasites and/or pathogens in the gastrointestinal tract of an animal or in animal feces comprising a container comprising label and a composition according to the present invention, wherein said label comprises instructions for use of the composition for inhibiting pathogen/parasite growth.

Typically, the system is present in the form of a package containing a composition of this invention, or in combination with packaging material. The packaging material includes a label or instructions for use of the components of the package. The instructions indicate the contemplated use of the package component as described herein for the methods or compositions of the invention.

For example, a system can comprise one or more unit dosages of a therapeutic composition according to the invention. Alternatively, the system can contain bulk quantities of a composition. The label contains instructions for using the composition in either unit dose or in bulk forms as appropriate, and may include information regarding storage of the composition, feeding instruction, health and diet indications, dosages, routes of administration, methods for blending the composition with pre-selected food stuffs, and the like information.

EQUIVALENTS

From the foregoing detailed description of the specific embodiments of the present invention, it should be readily apparent that a unique methodology for the utilization of lactic acid-producing bacteria, preferably *Bacillus coagulans*, for the prevention and treatment of gastrointestinal tract pathogens and their associated diseases, has been described.

Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For instance, the choice of the particular antibiotic which is utilized in the Therapeutic Composition of the present invention is believed to be a matter of routine for a person of ordinary skill in the art with knowledge of the embodiments described herein.

What is claimed is:

1. A method for reducing gastrointestinal colonization by a pathogenic *Candida* yeast, comprising identifying a mammalian subject having an infection with said pathogenic *Candida* yeast, and orally administering a therapeutically-effective concentration of *Bacillus coagulans* bacteria within a pharmaceutically-acceptable carrier suitable for administration to the gastrointestinal tract of said subject, wherein the *Bacillus coagulans* bacteria reduce colonization of the pathogenic *Candida* yeast.

2. The method of claim 1, wherein said *Candida* yeast is *Candida albicans* or *Candida tropicalis*.

3. The method of claim 1, further comprising the administration of a therapeutically-effective dose of an antibiotic.

4. The method of claim 3, wherein the bacteria are resistant to the antibiotic.

5. The method of claim 3, wherein the antibiotic is selected from the group consisting of a macrolide antibiotic, a cephalosporin antibiotic, a penicillin antibiotic, a fluoroquinolone antibiotic, and a vancomycin antibiotic.

6. The method of claim 3, wherein the antibiotic is selected from the group consisting of gentamicin, vancomycin, oxacillin, a tetracyclines, nitroflurantoin, chloramphenicol, clindamycin, trimethoprim-sulfamethoxasole, cefaclor, cefadroxil, cefixime, cefprozil, ceftriaxone, cefuroxime, cephalexin, loracarbef, ampicillin, amoxicillin/clavulanate, bacampicillin, cloxicillin, penicillin VK, ciprofloxacin, grepafloxacin, levofloxacin, lomefloxacin, norfloxacin, ofloxacin, sparfloxacin, trovafloxacin, azithromycin, and erythromycin.

7. The method of claim 1, wherein the bacteria are in the form of spores.

8. The method of claim 1, wherein the *Bacillus coagulans* is *B. coagulans* Hammer strain deposited under ATCC accession number 31284.

9. The method of claim 1, wherein approximately $2.5 \times 10^8$ to approximately $1 \times 10^{10}$ viable *Bacillus coagulans* bacteria or spores are administered per day.

10. The method of claim 1, wherein said mammalian subject is a human.

* * * * *